United States Patent
Boigegrain et al.

(10) Patent No.: US 6,482,986 B1
(45) Date of Patent: Nov. 19, 2002

(54) BENZENE DERIVATIVES, PREPARATION METHOD AND PHARMACEUTICAL COMPOSITIONS CONTAINING SAME

(75) Inventors: Robert Boigegrain, Assas (FR); Bernard Bourrie, Saint Gely du Fesc (FR); Martine Bourrie, Saint Gely du Fesc (FR); Pierre Casellas, Montpellier (FR); Jean Marc Herbert, Tournefeuille (FR); Pierre Lair, Goyrans (FR); Dino Nisato, Saint Georges d'Orques (FR); Raymond Paul, Saint Gely du Fesc (FR); Jean Claude Vernieres, Muret (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/009,140

(22) PCT Filed: Jun. 8, 2000

(86) PCT No.: PCT/FR00/01575

§ 371 (c)(1),
(2), (4) Date: Feb. 27, 2002

(87) PCT Pub. No.: WO00/76953

PCT Pub. Date: Dec. 21, 2000

(30) Foreign Application Priority Data

Jun. 11, 1999 (FR) ............................................. 99 07396

(51) Int. Cl.[7] ........................ C07C 211/00; A61K 31/35
(52) U.S. Cl. ..................... 564/337; 564/338; 564/339; 564/374; 564/383; 549/13; 549/426; 514/459; 514/432; 514/650; 514/654
(58) Field of Search ................................ 564/337, 338, 564/339, 374, 383; 549/13, 426; 514/459, 432, 650, 654

(56) References Cited

U.S. PATENT DOCUMENTS

| | | | |
|---|---|---|---|
| 5,231,092 A | 7/1993 | Lavastre et al. |
| 5,296,596 A | 3/1994 | Lavastre et al. |
| 5,354,781 A | 10/1994 | Breliere et al. |
| 5,449,639 A | 9/1995 | Breliere et al. |
| 6,235,791 B1 | 5/2001 | Breliere et al. |

FOREIGN PATENT DOCUMENTS

| | | |
|---|---|---|
| EP | 376850 | 7/1990 |
| EP | 461986 | 12/1991 |
| WO | WO 98/04251 | 2/1998 |

OTHER PUBLICATIONS

Bourrie et al., European Journal of Immunology, 25(10), pp. 2882–2887 (1985).
Paul et al., Journal of Neuroimmunology, 52(2), pp. 183–192 (1994).
Silve et al., Biology, 16(6), pp. 2719–2727 (1996).
Casellas et al., Journal of Neuroimmunology, 52(2), pp. 193–203 (1994).

*Primary Examiner*—Samuel Barts
(74) *Attorney, Agent, or Firm*—Michael D. Alexander; Paul E. Dupont

(57) ABSTRACT

The invention concerns compounds of formula (I) wherein A, X, Y, n, $R_1$, $R_2$ and $R_3$ are as defined in claim 1. Said compounds are specifically binding to sigma receptors particularly those of the peripheral nervous system.

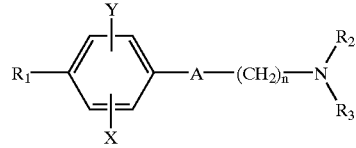

(I)

15 Claims, No Drawings

BENZENE DERIVATIVES, PREPARATION METHOD AND PHARMACEUTICAL COMPOSITIONS CONTAINING SAME

This application is a 371 of PCT/FR00/01575 filed Jun. 8, 2000.

The present invention relates to benzene derivatives comprising an amine function substituted with an alkyl group and a cycloalkyl group, which binds specifically to the sigma receptors, in particular to those of the peripheral nervous system, to a process for preparing these compounds and to their use in pharmaceutical compositions and more particularly as immunosuppressants.

The sigma receptors have been revealed with the aid of several ligands. Firstly, mention may be made of opiate compounds, 6,7-benzomorphans or SKF-10,047, more particularly the chiral compound (+) SKF-10,047 (W. R. Martin et al., J. Pharmacol. Exp. Ther. 1976,197, 517–532; B. R. Martin et al., J. Pharmacol. Exp. Ther. 1984, 231, 539–544). Among these compounds, the ones most commonly used are (+) N-allylnormetazocin or (+) NANM and (+) pentazocin. A neuroleptic agent, haloperidol, is also a sigma receptor ligand, as are (+) 3-(3-hydroxyphenyl)-1-propylpiperidine and (+) 3-PPP (B. L. Largent et al., Proc. Nat. Acad. Sci. USA 1984, 81, 4983–4987).

U.S. Pat. No. 4,709,094 describes guanidine derivatives that are highly active as ligands that are specific for the sigma receptors, and mention may be made more particularly of di-(O-tolyl)guanidine, or DTG. The anatomic distribution of the sigma receptors in the brain has been studied by autoradiography, after labelling these receptors with DTG according to E. Weber et al., Proc. Nat. Acad. Sci. USA 1986, 83, 8784–8788, as well as with the ligands (+) SKF-10,047 and (+) 3-PPP according to B. L. Largent et al., J. Pharmacol. Exp. Ther. USA 1986, 238, 739–748. The autoradiography study made it possible to identify the sigma receptors of the brain clearly and to distinguish them from the other opiate receptors, as well as from the phencyclidine receptors. The sigma receptors are particularly abundant in the central nervous system and are concentrated in the cerebral trunk, the limbic system and the regions involved in regulating the emotions. Sigma receptors are also found in various peripheral tissues. At least two types of sigma receptor are distinguished: the sigma-1 receptors and the sigma-2 receptors. Ligands of the (+) SKF-10,047 type bind selectively to the sigma-1 receptors, while other ligands such as DTG, haloperidol or (+) 3-PPP show great affinity for both the sigma-1 and sigma-2 receptors.

Patent EP 461 986 describes compounds of formula:

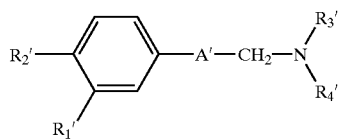

(A)

which bind selectively to the sigma receptors and which have immunosuppressant activity.

Among this series of compounds, (Z)-[3-(3-chloro-4-cyclohexylphenyl)allyl]cyclohexylethylamine hydrochloride, of formula:

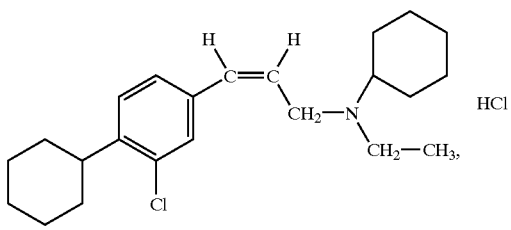

has been studied in particular. Reference may be made, for example, to Biological Chemistry 1997, 272 (43), 27107–27115; Immunopharmacology and Immunotoxicology 1996, 18 (2), 179–191. However, the compounds of formula (A) have a specific property which may be considered as a drawback. This is a property which appears during metabolization: the dependency on the cytochrome known as CYP 2D6.

In 1957, it was envisaged for the first time that hereditary differences might be responsible for variations in response to medicinal products. Oxidative metabolism shows large variations between individuals and races. The research carried out in the last 15 years has shown that the variations in the functional expression of the multigenic cytochrome P450 (CYP) family is the cause of these differences. Only a few isoforms of cytochrome P450 among those already characterized in man have a role in the oxidative metabolism of medicinal products. Reference may be made to Xenobiotica, 1986, 16, 367–378. Until now, CYP 1A2, CYP 2A6, CYP 2C9, CYP 2D6, CYP 2C19, CYP 2E1 and CYP 3A4 have been identified on the basis of their clinical importance. Currently, it is estimated that CYP 3A4, CYP 2D6 and CYP 2C9 are responsible by themselves (and to variable degrees) for 90% of the oxidative metabolism of medicinal products. Although the functional expression of these isoforms is regulated and influenced by a good number of environmental and physiological factors, the genetic factors have the most pronounced influence, which underlines the important role played by polymorphism in the oxidation of medicinal products. A certain number of these polymorphisms have been studied (particularly those of CYP 2C19 and CYP 2D6). More particularly, the clinical importance of the polymorphism of CYP 2D6 in the 4-hydroxylation of debrisoquine has been demonstrated (Clin. Pharmacol. Ther. 1991, 50, 233–238). The genetic polymorphism of CYP 2D6 is responsible for the problematic metabolism of more than 30 important medicinal products and affects up to 10% of the Caucasian population (slow metabolizers). It has now been shown that this isoform controls the biotransformation of medicinal products such as antiarrythmic agents, β-blockers, anti-hypertensive agents, antiangina agents, neuroleptic agents and antidepressants. With a few exceptions, these medicinal products are used in psychiatric and cardiovascular medicine for long-term treatment.

The pharmacokinetic consequences are especially of quantitative order: slow-metabolizing individuals have a level of unchanged product which is higher than the others. These quantitative differences have a considerable clinical impact for molecules which have a small therapeutic index.

Genetics thus greatly influences the differences in efficacy and in side effects observed between individuals. Thus, it is important to determine whether or not the metabolism of a medicinal product can be modified in the case of genetic deficiency of an enzyme.

Novel fine benzene derivatives for the sigma receptors, in particular those of the peripheral nervous system, have now been found according to the present invention, which have immunosuppressant activity but a low rate of metabolization and/or little or no involvement of CYP 2D6 in the oxidative process.

The compounds according to the invention also have antitumour activity, and in particular they inhibit the proliferation of cancer cells.

Moreover, these novel compounds have been shown to have activity in the cardiovascular field, more particularly in controlling the heart rate.

The compounds according to the invention also have activity on apoptosis.

Thus, according to one of its aspects, the present invention relates to the compounds of formula:

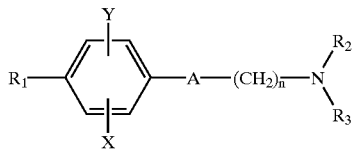

(I)

in which:
A represents a group chosen from the following:
—C≡C—, —CH═CH—; —CH$_2$—CH$_2$—
n is equal to 1 or 2;
X represents a hydrogen, chlorine or fluorine atom or a methyl or methoxy group;
Y represents a hydrogen atom or a chlorine or fluorine atom;
R$_1$ represents a cyclohexyl group monosubstituted, disubstituted, trisubstituted or tetrasubstituted with a methyl group; a phenyl group monosubstituted or disubstituted with a fluorine or chlorine atom or with a methoxy group; a cycloheptyl, tert-butyl, dicyclopropylmethyl, bicyclo[3.2.1]octanyl, 4-tetrahydropyranyl, 4-tetrahydrothiopyranyl or 1- or 2-adamantyl or adamantan-2-ol group; or R$_1$ represents a phenyl group, it being understood that, in this case, X and Y are other than hydrogen;
R$_2$ represents a hydrogen atom or a (C$_1$–C$_4$)alkyl group optionally substituted with a trifluoromethyl group;
R$_3$ represents a (C$_5$–C$_7$)cycloalkyl; and the addition salts of these compounds with pharmaceutically acceptable acids, as well as the solvates and hydrates thereof.

The term "alkyl" means a linear or branched, saturated, hydrocarbon-based monovalent radical. The term "(C$_1$–C$_4$) alkyl" means an alkyl radical comprising from 1 to 4 carbon atoms.

According to another of its aspects, the invention relates to the compounds of formula (I) in which:
A represents a group chosen from the following:
—C≡C—, —CH═CH—; —CH$_2$—CH$_2$—
n is equal to 1 or 2;
X represents a hydrogen, chlorine or fluorine atom or a methyl or methoxy group;
Y represents a hydrogen atom or a chlorine or fluorine atom;
R$_1$ represents a cyclohexyl group monosubstituted, disubstituted, trisubstituted or tetrasubstituted with a methyl group; a phenyl group monosubstituted or disubstituted with a fluorine or chlorine atom or with a methoxy group; a cycloheptyl, tert-butyl, dicyclopropylmethyl, bicyclo[3.2.1]octanyl, 4-tetrahydropyranyl, 4-tetrahydrothiopyranyl or 1- or 2-adamantyl group; or R$_1$ represents a phenyl group, it being understood that, in this case, X and Y are other than hydrogen;
R$_2$ represents a (C$_1$–C$_4$)alkyl optionally substituted with a trifluoromethyl group;
R$_3$ represents a (C$_5$–C$_7$)cycloalkyl; and the addition salts of these compounds with pharmaceutically acceptable acids, as well as the solvates and hydrates thereof.

According to another of its aspects, the invention relates to the compounds of formula:

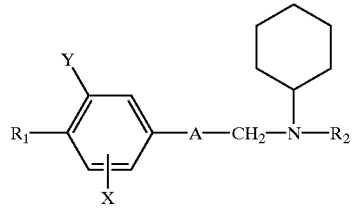

(I.1)

in which:
A represents a group chosen from the following:
—C≡C—; —CH═CH—; —CH$_2$—CH$_2$—
X represents a hydrogen or chlorine atom;
Y represents a hydrogen atom or a chlorine atom;
R$_1$ represents a cyclohexyl monosubstituted, disubstituted, trisubstituted or tetrasubstituted with a methyl group; a phenyl group substituted with a chlorine atom, a methoxy group or one or two fluorine atoms; a tert-butyl or 1- or 2-adamantyl group; or R$_1$ represents a phenyl group, it being understood that, in this case, X and Y both represent a chlorine atom;
R$_2$ represents a (C$_2$–C$_3$)alkyl; and the addition salts of these compounds with pharmaceutically acceptable acids, as well as the solvates and hydrates thereof.

According to another of its aspects, the invention relates to the compounds of formula (I) and (I.1) in which A represents a —CH═CH— group of (Z) configuration and the addition salts of these compounds with pharmaceutically acceptable acids, as well as the solvates and hydrates thereof. According to another of its aspects, the invention relates to the compounds as defined above in which X represents a chlorine atom and Y represents a hydrogen or chlorine atom, and the addition salts of these compounds with pharmaceutically acceptable acids, as well as the solvates and hydrates thereof.

According to another of its aspects, the invention relates to the compounds as defined above in which R$_1$ represents. a 3,3,5,5-tetramethylcyclohexyl or 3,3-dimethylcyclohexyl or 4,4-dimethylcyclohexyl group, a phenyl group monosubstituted or disubstituted with a fluorine atom or substituted in position 4 with a chlorine atom; or a 1- or 2-adamantyl group; and the addition salts of these compounds with pharmaceutically acceptable acids, as well as the solvates and hydrates thereof.

The following compounds:

[(Z)-3-(4-Adamantan-2-yl-3-chlorophenyl)propen-2-yl] cyclohexylethylamine;
[(Z)-3-(4-Adamantan-2-ylphenyl)propen-2-yl] cyclohexylethylamine;
{(Z)-3-[4-(4,4-Dimethylcyclohexyl)-2-chlorophenyl]propen-2-yl}cyclohexylethylamine;
[(Z)-3-(4-Adamantan-1-yl-3-chlorophenyl)propen-2-yl] cyclohexylethylamine;
[(Z)-3-(4-Adamantan-2-yl-3,5-dichlorophenyl)propen-2-yl] cyclohexylethylamine;
[(Z)-3-(4-Adamantan-2-yl-3,5-dichlorophenyl)propen-2-yl] cyclohexyl(2-methylethyl)amine;

as well as the salts thereof with pharmaceutically acceptable acids, the solvates and hydrates thereof constitute another aspect of the invention.

In particular, the invention relates to [(Z)-3-(4-adamantan-2-yl-3,5-dichlorophenyl)propen-2-yl] cyclohexylethylamine as well as the salts thereof with pharmaceutically acceptable acids, solvates and hydrates thereof.

The salts of the compounds according to the invention are prepared according to techniques that are well known to those skilled in the art.

The salts of the compounds of formula (I) according to the present invention comprise those with inorganic or organic acids which allow a separation or a suitable crystallization of the compounds of formula (I), as well as of the pharmaceutically acceptable salts. Suitable acids which may be mentioned are: picric acid, oxalic acid or an optically active acid, for example a tartaric acid, a dibenzoyltartaric acid, a mandelic acid or a camphorsulphonic acid, and those which form physiologically acceptable salts, such as the hydrochloride, hydrobromide, sulphate, hydrogen sulphate, dihydrogen phosphate, maleate, fumarate, 2naphthalene-sulphonate or para-toluenesulphonate. The hydrochlorides are most particularly preferred among the salts of the compounds of formula (I). When a compound according to the invention contains one or more asymmetric carbons, the optical isomers of this compound form an integral part of the invention. When a compound according to the invention presents a stereoisomerism, for example of axial-equatorial type or Z-E type, the invention comprises all the stereoisomers of this compound.

The present invention comprises the compounds of formulas (I) in the form of pure isomers, but also in the form of a mixture of isomers in any proportion. The compounds (I) are isolated in the form of pure isomers by the conventional separation techniques: use may be made, for example, of fractional recrystallizations of a salt of the racemic mixture with an optically active acid or base, the principle of which is well known, or conventional chromatography techniques on a chiral phase or a non-chiral phase; for example, use may be made of separation on silica gel or $C_{18}$-grafted silica gel, eluting with mixtures such as chlorinated solvents/alcohol. The above compounds of formula (I) also comprise those in which one or more hydrogen, carbon or halogen atoms, in particular chlorine or fluorine atoms, have been replaced with their radioactive isotope, for example tritium or carbon-14. Such labelled compounds are useful in research studies, of metabolism or pharmacokinetics, in biochemical tests as receptor ligands.

The functional groups which may be present in the molecule of the compounds of formula (I) and in the reaction intermediates can be protected, either in permanent form or in temporary form, with protecting groups which ensure an unequivocal synthesis of the expected compounds. The protection and deprotection reactions are carried out according to techniques that are well known to those skilled in the art. The expression "temporary protecting group for amines, alcohols, phenolthiols or carboxylic acids" means protecting groups such as those described in Protective Groups in Organic Synthesis, Greene T. W. and Wuts P. G. M., ed. John Wiley and Sons, 1991 and in Protecting Groups, Kocienski P. J., 1994, Georg Thieme Verlag. A person skilled in the art will be capable of selecting the appropriate protecting groups. The compounds of formula (I) can comprise precursor groups for other functions which are generated subsequently in one or more steps.

A subject of the present invention is also a process for preparing the compounds of formula (I), characterized in that:

1) when A represents a —C≡C— group:
   a) either, if n=1, a Mannich reaction is carried out between the phenylacetylene derivative of formula:

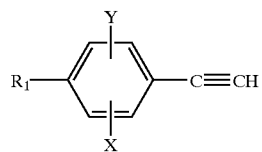

(II)

in which $R_1$, X and Y are as defined for (I), the formaldehyde and the amine (1) $HNR_2R_3$, $R_2$ and $R_3$ being as defined for (I);

b) or, a Suzuki coupling is carried out between the compound of formula:

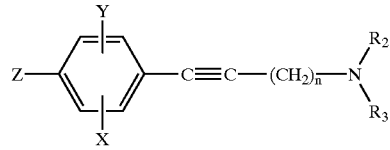

(Ia)

in which X, Y, n, $R_2$ and $R_3$ are as defined for (I) and Z represents a bromine, an iodine or a trifluoromethanesulphonate (OTf) group and a boron derivative (2) of formula $R_1$—$B(OR)_2$ in which R represents a hydrogen atom or an alkyl or aryl group in the presence of a base and a metal catalyst;

c) or, when $R_1$ represents a cyclohexyl group monosubstituted, disubstituted, trisubstituted or tetrasubstituted with a methyl group; a cycloheptyl, 4-tetrahydropyranyl, 4-tetrahydrothiopyranyl or adamantyl group, a coupling is carried out between compound (Ia) in which Z represents an iodine or bromine atom and the ketone (3) corresponding to $R_1$ represented by

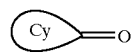

in the presence of a base, to give the intermediate compound of formula:

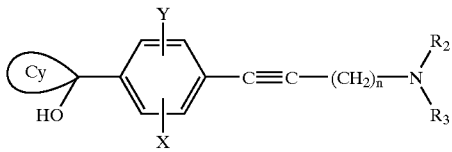

(I')

in which X, Y, n, $R_2$ and $R_3$ are as defined for (I); the said compound (II) then being reduced under selective conditions;

d) or, a coupling reaction is carried out between the amine of formula:

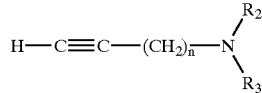

(4)

in which n, $R_2$ and $R_3$ are as defined for (I), and the compound of formula:

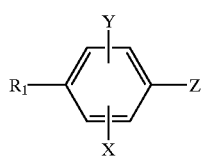
(III)

in which $R_1$, X and Y are as defined for (I) and Z represents a bromine or iodine atom or a trifluoromethylsulphonate (triflate or OTf) group;

2) when A represents a —CH═CH— group, a hydrogenation is carried out, with nascent hydrogen or in the presence of cyclohexene, of compound (I) in which A represents an acetylene group —C≡C—, in order to prepare the ethylenic compound (I) in the form of a mixture of the Z and E isomers, or this hydrogenation is carried out in the presence of a metal catalyst on a support in order to prepare the ethylenic compound (I) in Z form, or alternatively compound (I) in which A represents an acetylene group —C≡C— is reacted with a metal hydride in order to prepare the ethylenic compound (I) in E form;

3) when A represents a —CH$_2$—CH$_2$— group, a hydrogenation is carried out on compound (I) in which A represents a —CH═CH— or —C≡C— group.

Step 1a of the process according to the invention is carried out with heating, preferably at a temperature of between 80° C. and 90° C., in a polar solvent such as 1,2-dimethoxyethane or 1,4-dioxane. A catalyst can be used to facilitate the condensation reaction, for example a metal salt such as copper II chloride or copper III chloride.

In step 1b of the process, the Suzuki coupling is preferably carried out between a compound (Ia) in which Z represents OTf and the boron derivative (2) of formula $R_1$—B(OH)$_2$. The reaction is carried out in the presence of a base, such as alkali metal or alkaline-earth metal hydroxides, alkoxides, phosphates or carbonates, more particularly potassium phosphate or sodium carbonate. The reaction is carried out in the presence of a metal catalyst, for example a copper, tin or, preferably, palladium catalyst, such as tetrakis(triphenylphosphine)palladium optionally with a halide such as lithium chloride acting as co-catalyst. The process is performed with heating, at a temperature of between 60° C. and 80° C. in an inert solvent such as toluene or 1,2-dimethoxethane or, preferably, in a toluene/aqueous solution two-phase medium optionally with a portion of alcohol such as ethanol. Suzuki coupling has been studied in many publications such as, for example, Synth. Commun. 1981, 11 (7), 513–519 and J. Org. Chem. 1993, 58 (8), 2201–2208. The boronic acids (2) $R_1$—B(OH)$_2$ are commercially available or synthesized conventionally from the corresponding halo, preferably bromo, derivatives $R_1$Br by the action, for example, of trimethyl borate in the presence of a base such as tert-butyllithium.

In step 1c, the coupling is preferably carried out on a compound (Ia) in which Z represents a bromine atom, in the presence of a base such as n-butyllithium in an inert solvent, preferably diethyl ether at low temperature, the preferred temperature range being from −80 to −70° C. The reduction of (I') to (I) is carried out under selective conditions, for example according to the method described in Tetrahedron, 1995, 51, 11043–11062 by the action of chlorotrimethylsilane and sodium iodide in a mixture of acetonitrile/chlorinated solvent such as dichloromethane, followed by a treatment with acetic acid in the presence of zinc, or alternatively by the action of hydriodic acid or by ionic hydrogenation by the action of sodium tetraborohydride in triflic acid.

In step 1d of the process, the coupling is carried out in the presence of a palladium catalyst, one or more tertiary amines and optionally lithium chloride. A compound (III) in which Z represents a triflate will preferably be used, and the process will be carried out in the presence of a palladium catalyst such as tetrakis(triphenylphosphine)palladium or dichlorobis(triphenylphosphine)palladium and optionally a co-catalyst such as copper iodide. When Z represents a triflate, lithium chloride will also be used. This coupling is preferably carried out in the presence of triethylamine and pyridine at the reflux point of the reaction mixture. For this type of coupling, known as Sonogashira coupling, reference may be made to J. Org. Chem. 1993, 58, 7368–7376 and 1998, 63, 1109–1118; Syn. Lett. 1995, 1115–1116 and Synthesis, 1987, 981.

To prepare the compounds (I) in which A represents a —CH═CH— group in Z form, the hydrogenation is generally carried out in the presence of cyclohexene and a metal catalyst on a support, such as palladium on barium sulphate or calcium carbonate or Raney nickel or, preferably, the Lindlar catalyst, in a solvent which is inert for the reaction, such as petroleum ether or an alcoholic solvent. To prepare the compounds (I) in E form, the metal hydride preferably used is diisobutylaluminium hydride (DIBALH) in an inert solvent such as toluene.

To prepare the compounds (I) in which A represents a —CH$_2$—CH$_2$—group, the hydrogenation is generally carried out in an alcohol, for example ethanol, in the presence of a catalyst such as platinum oxide or, preferably, palladium on charcoal.

For the techniques for reducing the alkenes and alkynes used above, reference may be made to "Catalytic Hydrogenation. Techniques and Applications in Organic Chemistry", Robert L. Augustine, 1965, Marcel Dekker, Inc. New York.

The general process for preparing the compounds (I) in which A represents an acetylene group —C≡C— is described in Scheme 1 below:

SCHEME 1

ROUTE A
if n = 1

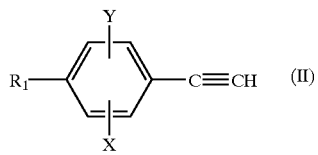 (II)

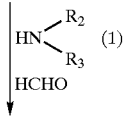

ROUTE B
if n = 1

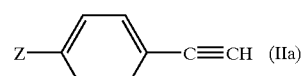 (IIa)

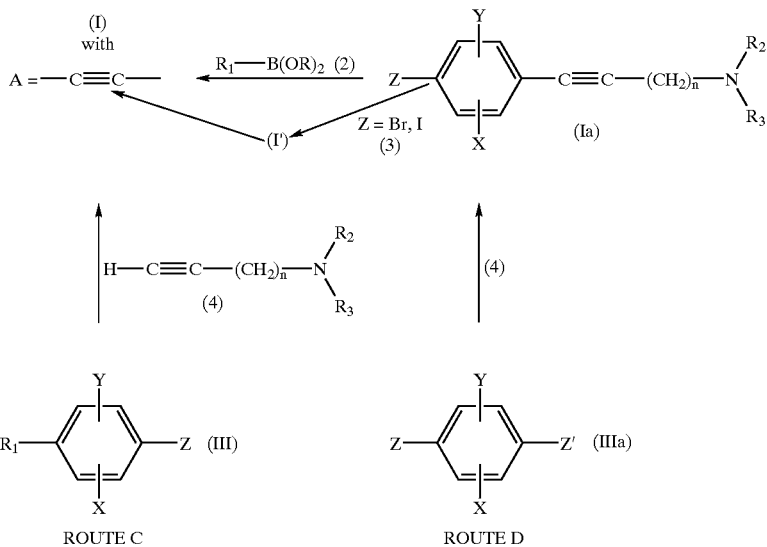

In Scheme 1, A═—C≡C—, and X, Y, n, $R_1$, $R_2$ and $R_3$ are as defined for (I), R represents a hydrogen atom or an alkyl or aryl group, Z represents a bromine or iodine atom or a triflate and Z' represents a triflate when Z represents a bromine or iodine, or else Z' represents a bromine or iodine atom. The importance of the nature of the substituents Z and Z' in the coupling reaction labelled ROUTE D will be detailed hereinbelow.

Compound (II) is obtained by treatment in basic medium of the chloroacrolein of formula:

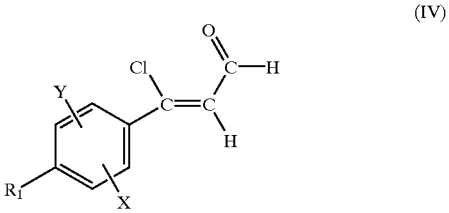

in which X, Y and $R_1$ are as defined for (I), preferably by the action of sodium hydroxide in a solvent such as tetrahydrofuran or, preferably, 1,4-dioxane, at the reflux temperature of the solvent.

The chloroacrolein (IV) is prepared from the acetophenone of formula:

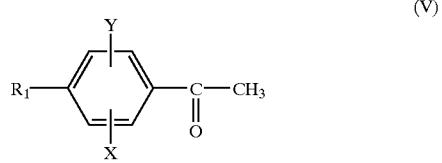

in which X, Y and $R_1$ are as defined for (I), by the action of a Vilsmeier complex. Use is made, for example, of (chloromethylene)dimethylammonium chloride, a commercial Vilsmeier complex, or of a Vilsmeier complex obtained from a disubstituted formamide combined with oxalyl chloride, phosphorus oxychloride or phosgene. The process is generally performed in a chlorinated solvent or an ether at a temperature of between −20° C. and 40° C. A Vilsmeier complex obtained from dimethylformamide and oxalyl chloride in a solvent such as dichloromethane or 1,2-dimethoxyethane at temperatures of between −10° C. and 10° C. is used more particularly.

For this type of reaction, reference may be made, for example, to J. Chem. Soc. (C) 1970, 2484–2488 and Angew. Chem. Internat. Ed. 1963, 2, 98–99.

The acetophenones (V) are known or prepared according to known methods such as those described in Gazz. Chim. Ital. 1949, 79, 453–457 and J. Am. Chem. Soc. 1947, 69, 1651–1652.

Scheme 2 illustrates the methods used to prepare the compounds (V).

SCHEME 2

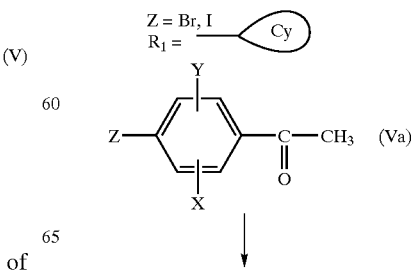

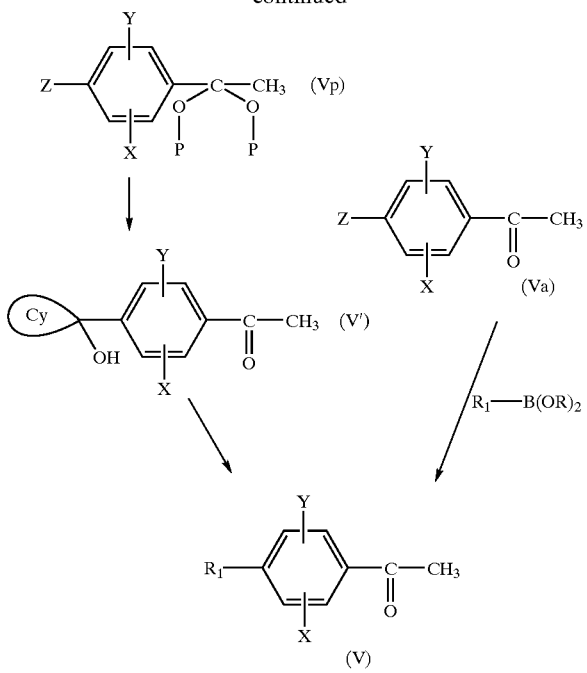

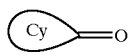

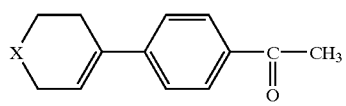

In Scheme 2, X, Y and $R_1$ are as defined for (I), Cy is as defined above for (I'), Z represents a bromine or iodine atom or OTf, R represents a hydrogen atom or an alkyl or aryl group and P represents a protecting group for the ketone function such as a methyl.

The compounds (V) can be obtained directly from the compounds (Va) by the action of the boron compound $R_1$—$B(OR)_2$ (2) as described for the conversion from (Ia) to (I). The ketone function of the compound (Va) can also be protected conventionally, for example by the action of a trialkyl orthoformate in the corresponding alcohol in the presence of an acid such as para-toluenesulphonic acid.

The compound (Vp) is thus obtained, which is reacted with the ketone

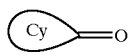

under the conditions described for the conversion from (Ia) to (I'). The ketone function is deprotected by hydrolysis in acidic medium to give the compound (V'). The said compound (V') is then reduced under the mild conditions described for the conversion of (I') to (I).

In certain cases, for example when R, represents a 4,4-dimethylcyclohexyl or 4-tetrahydropyranyl group, the intermediate compound of formula:

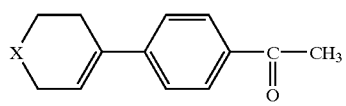

in which X=O or —$C(CH_3)_2$ may be formed, which will give, after prior protection of the ketone function and hydrogenation, for example in the presence of palladium on charcoal in methanol, followed by deprotection of the ketone function, the desired compound (V).

The compounds (V) in which X and/or Y is other than hydrogen can be obtained from the compounds (V) in which X=Y=H by methods known to those skilled in the art. For example, when X and/or Y represents a chlorine atom, chlorination of the aromatic nucleus is carried out by the action of gaseous chlorine in the presence of a Lewis acid, preferably aluminium trichloride, in a chlorinated solvent such as dichloromethane, preferably at 0° C.

The compounds (Va) are commercially available or can be prepared according to methods known to those skilled in the art.

For example, when Z represents a triflate, the compound (Va) can be prepared as shown in SCHEME 3:

SCHEME 3

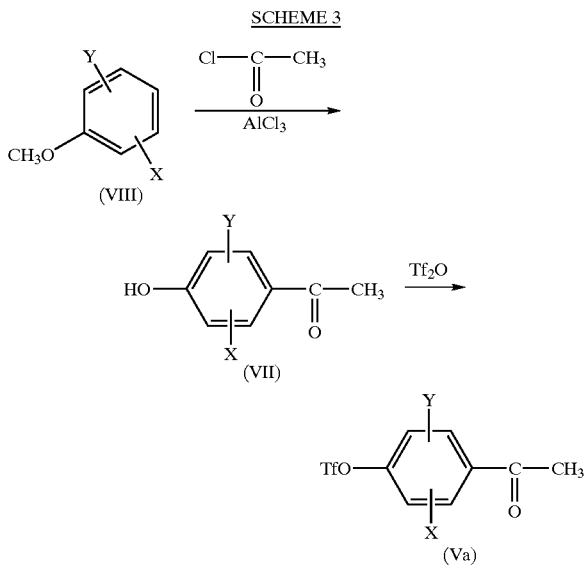

In Scheme 3, X and Y are as defined for (I). The compounds (VIII) are commercially available or prepared conventionally.

According to another of its aspects, a subject of the present invention is also the compounds of formula (Ia):

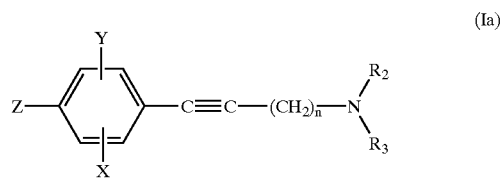

in which X, Y, n, $R_2$ and $R_3$ are as defined for (I) and Z represents a bromine or iodine atom or OTf. These compounds are novel and constitute key intermediates in the synthesis of the compounds (I).

The present invention also relates to a process for preparing the derivatives (Ia) characterized in that:
  either, when n=1, a Mannich reaction is carried out between the phenylacetylene derivative of formula:

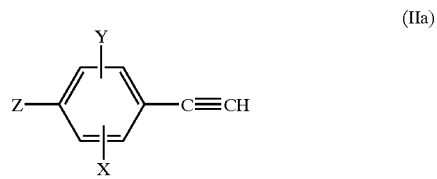

in which X and Y are as defined for (I) and Z represents a bromine or iodine atom or OTf, formaldehyde and the amine (1) $HNR_2R_3$, or, a coupling reaction is carried out between the amine of formula:

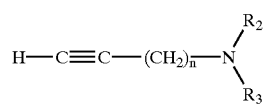

(4)

in which $R_2$, $R_3$ and n are as defined for (I), and the derivative of formula:

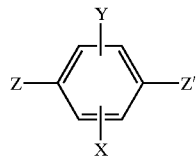

(IIIa)

in which X and Y are as defined for (I), Z represents a bromine or iodine atom or a triflate and Z' represents a bromine or iodine atom if Z represents a triflate, otherwise Z' represents a triflate, in the presence of a palladium catalyst, one or more tertiary amines and optionally lithium chloride.

The Mannich reaction is carried out under the same conditions as those described for the conversion from (II) to (I).

A Sonogashira reaction described for the coupling of the compounds (III) and (4) is used for the coupling between the compounds (IIIa) and (4). When Z represents a triflate and Z' represents a bromine or iodine atom, the process is performed in the absence of lithium chloride. On the other hand, when Z represents a bromine or iodine atom and Z' represents a triflate, the process is performed in the presence of lithium chloride. The use of lithium chloride makes it possible to direct the coupling reaction.

The propargylamines (4) (in the case where n=1) are prepared conventionally, for example according to Tetrahedron Lett. 1989, 30 (13), 1679–1682 starting with the amine (1) $HNR_2R_3$ and 3-bromopropyne by the action of potassium carbonate in acetonitrile at a temperature of between 50° C. and 80° C.

The compounds (III) in which Z=OTf are conventionally obtained from the corresponding alcohols of formula:

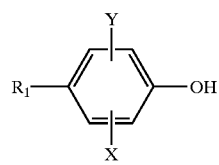

(IX)

in which X, Y and $R_1$ are as defined for (I), by the action of trifluoromethanesulphonic anhydride (triflic anhydride) in pyridine.

The alcohols (IX) are themselves obtained from the compounds of formula:

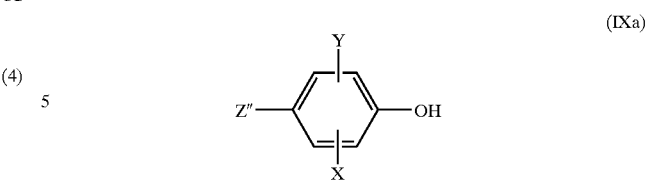

(IXa)

in which Z" represents a bromine or iodine atom, according to the methods described previously for the conversion from (Ia) to (I) or from (Va) to (V). The compounds (IXa) are commercially available or prepared according to techniques that are well known to those skilled in the art.

The compound (IIa) is prepared from the chloroacrolein of formula:

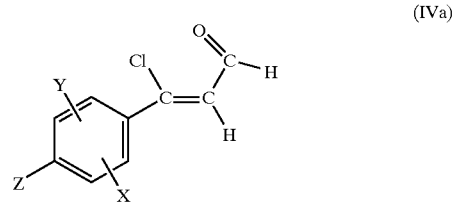

(IVa)

dans laquelle X and Y are as defined for (I) and Z represents a bromine or iodine atom or OTf, which is itself obtained from the acetophenone of formula:

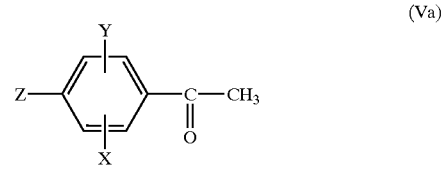

(Va)

in which X, Y and Z are as defined above for (IVa), according to the methods described for the conversion from (IV) to (II) and from (V) to (IV).

The compounds according to the invention have undergone biochemical and pharmacological studies. The compounds of formula (I) and the pharmaceutically acceptable salts, hydrates and solvates thereof bind specifically to the sigma receptors, in particular to those of the peripheral nervous system, also known as the sigma-2 receptors.

The affinity for the sigma-1 receptors was studied in vitro on guinea pig brain membranes using $^3$H-(+)-3PPP as ligand, according to De Haven-Hudkins et al., Life Science 1993, 53, 41–48. (+)-Pentazocin binds specifically to the sigma-1 receptors. A guinea pig brain membrane fragment is prepared according to the usual methods. The membrane preparation (0.3 mg of protein/ml) is incubated for 150 minutes at 37° C. in the presence of 0.5 nM [$^3$H]-(+)-pentazocin. The non-specific binding is determined in the presence of 10 μM (+)-pentazocin. The membranes are then filtered and rinsed 3 times. The filtered material is analysed to determine the fraction of [$^3$H]-pentazocin specifically bound. Under these conditions, the compounds of the invention, examples of which follow, have $IC_{50}$ values of between 0.1 nM and 100 nM.

The capacity of the compounds according to the invention to interact with the sigma-2 receptors was tested in vitro on the rat spleen membranes using [$^3$H]-DTG as ligand, according to R. Paul et al. Journal of Neuroimmunology 1994, 52, 183–192. The membrane preparation (1 ml) is incubated with 2 nM [³H]-DTG for 90 minutes at 20° C. The amount of non-specific binding is estimated in the presence of 10 µM DTG or haloperidol. The membranes are filtered and washed twice, and the filtered material is analysed to determine the amount of [³H]-DTG specifically bound. The compounds according to the invention have a sigma-2 activity of between 1 nM and 500 nM.

1—The Compounds According to the Invention were also Tested in Tests of Immunosuppressant Activity Presented Below D-Galactosamine, SEB and LPS are obtained from Sigma Chemical Co (St Louis, Mo.). The SEB contains less than 0.00029% of endotoxin ("limulus amoebocyte lysate" test Bioproduct, Walkersville, Md.). These molecules are dissolved in a phosphate salt buffer solution; the compounds according to the invention are dissolved in a solution containing 5% ethanol, 5% Tween 80 and 90% water.

The mice used are 6- to 8-week-old female Balb/C mice obtained from the Charles River breeding stock (France) and 8-week-old female C57BL/6 and B6D2F1 mice obtained from the IFFA CREDO breeding stock (Domaine des Oncins, BP 0109, 69592 L'Arbresle Cedex, France).

Cytokine determination: 5 mice are injected with the compounds or the solvent alone, intraperitoneally 30 minutes before the LPS (10 µg/mouse intravenously) or orally 1 hour before. Blood samples are taken by retro-orbital or cardiac puncture, 1 hour 30 minutes after the injection of LPS. The samples are centrifuged and the serum is taken. The serum is stored at −80° C. before analysis. The TNF-□ and IL-10 contents are determined with the aid of the ELISA kit (Genzyme, Cambridge). The tests are carried out according to the instructions featured on the notice for use.

Toxin shock: the compounds are administered intraperitoneally to 10 animals. 30 minutes later, SEB (*Staphylococcus enterotoxin* B, Sigma St. Louis, Mo.) is administered at a rate of 10 µg/mouse intravenously, and D-galactosamine is administered (20 mg/mouse, intraperitoneally).

Death is observed 48 hours later.

GVH (Graft-Versus-Host) disease: the test compounds or the solvent alone (as control) are injected into female B6D2F1 (H2$^b$×H2$^d$) mice intraperitoneally. 4 hours later, they are injected with 7.5×10⁷ C57BL/6 (H2$^b$) mouse spleen mononuclear cells to initiate the GVH. All the animals are sacrificed one week after the graft and the increase in the weight of their spleen, caused by GVH, is measured.

The following index is $$\text{calculated: } I = \frac{\text{weight of the spleen}}{\text{weight of the animal}} \Big/ \frac{\text{weight of the spleen}}{\text{weight of the animal}}$$

The results are expressed as follows: $PS = \frac{Iexp - 1}{Icontr - 1} \times 100$ with *PS*: percentage of splenomegaly.

Measurement of the T cell proliferation: Cell suspensions are prepared using Balb/C mouse spleens. The red blood cells are first lysed in the course of a short hypotonic shock carried out with sterile distilled water. The remaining cells (the white blood cells) are washed twice with the culture medium (RPMI 1640 containing 2% heat-inactivated foetal calf serum, 2 mM L-glutamine, 1 mM sodium pyruvate, 100 UI/ml of penicillin, 100 µg/ml of streptomycin and 15 mM PIPES) adjusted beforehand to pH 6.6. The cell viability, determined using the trypan blue technique, always exceeds 95% by this preparation method.

The splenocytes, at a concentration of 6×10⁶ cells/ml, are cultured with the test products, in flat-bottomed 96-well plates (Falcon, Becton Dickinson, Lincoln Park, N.J.) in the presence of 2 µg/ml of SEB. Four wells are prepared for each concentration of test products. The incubation is carried out at 37° C. in a cell culture incubator (atmosphere: 95% air+5% CO₂) for 4 days. 2 µCi of tritiated thymidine (Amersham, Les Ullis, France) are then added to each culture well. Four hours later, the cells are recovered on a glass fibre filter (Filtermat A, Wallac, Turku, Finland) using a skatron (Pharmacia LKB, Piscataway, N.J.). The radioactivity incorporated and bound on the filter is measured in a suitable liquid scintillation counter (Betaplate, Pharmacia LKB).

The compounds according to the invention thus show immunosuppressant activity according to the results observed during these biochemical and behavioural tests.

2—The Compounds According to the Invention also Underwent Tests Showing their Capacity to Inhibit the Proliferation of Tumour Cells and Cancer Cells Measurement of the proliferation of MDA/MB231 cells (hormone-independant breast cancer): The MDA/MB231 cells are maintained in vitro by successive passages in DMEM medium (Gibco Laboratories, Grand Island, N.Y.) containing 10% heat-inactivated foetal calf serum, 1 mM sodium pyruvate, 100 UI/ml penicillin and 100 µg/ml of streptomycin.

For the proliferation measurement, the cells, at a concentration of 2×10⁵/ml, are cultured with the test products in RPMI 1640 medium containing 10 µg/ml of bovine insulin (Sigma) and 10 µg/ml of apotransferrin (Sigma), in flat-bottomed 96-well plates (Falcon, Becton Dickinson, Lincoln Park, N.J.). Three wells are prepared for each concentration of the test products. The incubation is carried out at 37° C. in a cell culture incubator (atmosphere: 95% air+5% CO₂) for 4 days. 2 µCi of tritiated thymidine (Amersham, Les Ullis, France) are then added to each culture well. Twenty-four hours later, the cells are detached using trypsin-EDTA (Gibco) and recovered on a glass fibre filter (Filtermat A, Wallac, Turku, Finland) using a skatron (Pharmacia LKB, Piscataway, N.J.). The radioactivity incorporated and bound on the filter is measured in a suitable liquid scintillation counter (Betaplate, Pharmacia LKB).

3—The Compounds of the Invention also Underwent Tests Demonstrating their Value in the Cardiovascular Field The antiarrhythmic effects of the compounds according to the invention were tested on reinfusion arrhythmias in anaesthetized rats. The experiment was performed on male Sprague Dawley rats under normal tension, weighing from 250 to 300 g. These animals are obtained from the IFFA CREDO breeding stock. The animals are kept under standard laboratory conditions and fed with standard food: AO4 (UAR). Water is supplied ad libitum. The occlusion and reinfusion technique used in this study corresponds to the methods described by Manning et al. (Circ. Res. 1984, 55, 545–548) and Kane et al. (Br. J. Pharmacol. 1984, 82, 349–357), slightly modified.

The animals were anaesthetized with pentobarbital sodium in a proportion of 60 mg/kg intraperitoneally, tracheotomized and ventilated with ambient air (Harward respirator). A catheter (PE10) was placed in the jugular vein for the intravenous injection of the test products. Hypodermic needles were placed on the four legs of the animal to record the electrocardiogram (ECG), usually DII (Gould ES1000 or on an Astromed 7400 polygraph). After performing a thoracotomy, a thread was placed on the left anterior descending coronary artery, near to its origin, to ligate the artery. The two ends of the thread are passed through a plastic tube, which is placed on the surface of the heart, just above the coronary artery. The coronary artery was occluded by exerting a tension on the ends of the thread for 5 minutes, and reinfusion was carried out by relaxing the tension. The temperature of the animal was controlled and maintained at 37° C. by means of a homeothermal cover.

For the intravenous-route study, the products were dissolved in a mixture of 75% PEG-400/distilled water and injected 5 minutes before ligating the artery. The products were injected in a volume of 0.1 ml/100 g of rat. The control group received this solvent.

For the oral-route study, the products were suspended in 0.6% methylcellulose and administered to the conscious animal by gavage, 120 minutes before ligating the coronary artery. The products were administered in a volume of 1 ml/100 g of rat. The control group received this vehicle.

The following arrhythmias were analysed by ECG during the reinfusion period (study lasting 10 minutes), according to the Lambeth Conventions (Cardiovasc. Res., 1988, 22, 447–455)

ventricular extrasystoles (VES),
ventricular tachycardia (TV), given that the VT is the succession of at least four VESs,
ventricular fibrillation (VF),
and mortality by fatal ventricular fibrillation or by cardiac arrest.

These arrhythmias are expressed as a percentage of animals exhibiting the event (frequency).

The animals were divided into groups of 4 to 10 animals. Each animal received only one dose of product. Both intravenously and orally, the products protect the animal against reinfusion arrhythmias by reducing or eliminating the mortality and frequency of the VFs. Furthermore, certain products reduce and/or eliminate the frequency of the VTs and the VESs, when they are administered intravenously.

The involvement of CYP 2D6 can be demonstrated by in vitro metabolism studies on human hepatic microsomal fractions. The concept most commonly used is inhibition of the enzyme by its specific inhibitor: quinidine used at 20 times its $K_i$ value, the $K_i$ being the absolute value of the inhibition constant of an active principle with respect to an enzyme.

Various models make it possible to demonstrate, in a specific metabolic reaction, the involvement of CYP 2D6.

It is possible to use human hepatic microsomal fractions which contain all of the human hepatic isoforms incubated in the presence of oxidoreduction co-factor (NADPH) and in the absence or presence of quinidine at 20 times its $K_i$ value with respect to CYP 2D6. The decrease in metabolization observed in the presence of quinidine may be associated with the inhibition of CYP 2D6 isoform, thus proving its possible involvement in the metabolic pathway(s) studied.

Microsomal fractions prepared from transfected cells which express only one isoform of human cytochrome P-450 (GENTEST Corp.) can also be used.

Human hepatocytes in primary culture which are capable of carrying out phase I and II metabolic reactions can also be used. In this case, the incubations are performed kinetically over 24 hours in the presence and absence of quinidine, a powerful and specific inhibitor of CYP 2D6.

Reference may be made to J. Pharm. Exp. Ther. 1996, 277, 321–332.

The compounds according to the invention were particularly studied as follows:

The said compound is incubated with human hepatic microsomal fractions and NADPH (oxidoreduction co-factor) as well as in the presence or absence of quinidine. The degree of inhibition of the metabolization observed in the presence of quinidine reflects the involvement of CYP 2D6 in the metabolization of the said compound. This approach can be used when the metabolization on hepatic microsomal fractions is of a sufficient amplitude (i.e. greater than or equal to 10% of the amount of starting substrate).

When the metabolization of the said compound on hepatic microsomes is too small to be able to quantify an inhibition with precision, or when additional verifications are necessary, additional, more in-depth studies on human hepatocytes in primary culture are performed kinetically over 24 hours. The degree of involvement of CYP 2D6 in the overall hepatic metabolization is then revealed by the decrease in the intrinsic clearance of the said compound, possibly observed in the presence of quinidine.

The results obtained show that the compounds according to the invention have a low degree of metabolization and/or little involvement of CYP 2D6 in the oxidation process.

No sign of toxicity is observed with these compounds at the pharmacologically active doses and their toxicity is thus compatible with their use as medicinal products.

The compounds of the present invention are particularly advantageous and may be used advantageously as medicinal products especially for treating conditions in which it is desirable to reduce the immunological activity, and also conditions associated with inflammatory disorders. Mention may be made, as non-limiting guide, of: conditions with autoimmune components such as, for example, rheumatoid arthritis, lupus erythematosus, conditions caused by demyelinization, for instance multiple sclerosis, Crohn's disease, atopic dermatitis, diabetes or graft rejection reactions, graft-versus-host reaction, organ transplant conditions, or alternatively autoimmune uveitis, uveoretinitis, Behcet's disease, atherosclerosis, asthma, fibrotic diseases, pulmonary idiopathic fibrosis, cystic fibrosis, glomerulonephritis, certain spondylarthropathies, rheumatoid spondylitis, osteoarthritis, gout, bone and cartilage resorption, osteoporosis, Paget's disease, septic shock, septicaemia, endotoxin shock, adult respiratory distress syndrome, silicosis, asbestosis, pulmonary sarcoidosis, ulcerative colitis, amyotrophic lateral sclerosis, Alzheimer's disease, Parkinson's disease, disseminated lupus erythematosus, haemodynamic shock, ischaemic pathologies (myocardial infarction, myocardial ischaemia, coronary vasospasm, angina pectoris, cardiac insufficiency, heart attack), post-ischaemic reinfusion attacks, malaria, mycobacterial infections, meningitis, leprosy, viral infections (HIV, cytomegalovirus, herpesvirus), AIDS-related opportunist infections, tuberculosis, psoriasis, atopic dermatitis and contact dermatitis, cachexia and radiation-related damage.

The compounds according to the invention can also be used in therapy in any pathological process which entails the proliferation of tumour cells. This cell proliferation can be either hormone-sensitive or hormone-insensitive. More specifically, clinical applications for which the use of these compounds may be envisaged comprise conditions resulting from a proliferation of tumour cells, in particular glioblastomas, neuroblastomas, lymphomas, myelomas, melanomas, leukaemia, carcinomas of the colon, and colorectal, epithelial, hepatic, pulmonary, mammary, ovarian, pancreatic, bladder or prostate carcinomas. The compounds according to the invention may thus be used advantageously as medicinal products intended to combat the proliferation of tumour cells, in particular as antitumour agents or anticancer agents.

They may also be used in the cardiovascular field, more particularly for treating heart rate disorders. The compounds according to the invention may also be very advantageous for their neuroprotective activity as well as their activity on apoptosis.

The use of the compounds according to the invention to treat the conditions mentioned above, as well as for the preparation of medicinal products intended to treat the said conditions, forms an integral part of the invention.

A subject of the present invention is thus also pharmaceutical compositions containing a compound according to the invention or a pharmaceutically acceptable salt, solvate or hydrate thereof, and suitable excipients.

The said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal, rectal or intraocular administration, the active principles of formula (I) above, or the possible salts, solvates or hydrates thereof, can be administered in unit administration forms, mixed with conventional pharmaceutical supports, to animals and human beings for the prophylaxis or treatment of the above disorders or conditions. The appropriate unit forms of administration comprise oral-route forms such as tablets, gel capsules, powders, granules and oral solutions or suspensions, sublingual, buccal, intratracheal and intranasal administration forms, subcutaneous, intramuscular or intravenous administration forms and rectal administration forms. For topical application, the compounds according to the invention can be used in creams, ointments, lotions or eyedrops.

In order to obtain the desired prophylactic or therapeutic effect, the dose of active principle can range between 0.2 mg and 15 mg per kg of body weight and per day.

Each unit dose can contain from 10 mg to 300 mg, preferably from 25 mg to 75 mg, of active ingredients in combination with a pharmaceutical support. This unit dose can be administered 1 to 5 times a day so as to administer a daily dosage of from 10 mg to 1500 mg, preferably from 25 mg to 375 mg.

When a solid composition in the form of tablets is prepared, the main active ingredient is mixed with a pharmaceutical vehicle, such as gelatin, starch, lactose, magnesium stearate, talc, gum arabic or the like. The tablets can be coated with sucrose, with a cellulosic derivative, or with other suitable materials, or alternatively they can be treated such that they have a prolonged or delayed activity and such that they release a predetermined amount of active principle continuously.

A preparation in gel capsules is obtained by mixing the active ingredient with a diluent and pouring the mixture obtained into soft or hard gel capsules. A preparation in the form of a syrup or elixir or for administration in the form of drops can contain the active ingredient together with a sweetener, preferably a calorie-free sweetener, methyl paraben and propyl paraben as antiseptic, as well as a flavour enhancer and a suitable dye.

The water-dispersible powders or granules can contain the active ingredient mixed with dispersants, wetting agents or suspending agents, such as polyvinylpyrrolidone, as well as with sweeteners or flavour enhancers.

For rectal administration, use is made of suppositories which are prepared with binders melting at rectal temperature, for example cocoa butter or polyethylene glycols.

For parenteral administration, use is made of aqueous suspensions, isotonic saline solutions or injectable sterile solutions which contain pharmacologically compatible dispersants and/or wetting agents, for example propylene glycol or butylene glycol.

The active principle can also be formulated in the form of microcapsules, optionally with one or more supports or additives, or alternatively with matrices such as a polymer or a cyclodextrin (patch, sustained-release forms).

The compositions of the present invention can contain, along with the products of formula (I) above or the pharmaceutically acceptable salts, solvates and hydrates thereof, other active principles which can be used in the treatment of the complaints or conditions indicated above.

Thus, a subject of the present invention is also pharmaceutical compositions containing several active principles in combination, one of which is a compound according to the invention.

The PREPARATIONS and EXAMPLES below illustrate the invention without, however, limiting it. The melting points are measured according to the Micro-köfler technique.

The nuclear magnetic resonance spectra were acquired in dimethyl sulphoxide except where otherwise mentioned, at 200 MHz, and the chemical shifts are expressed in ppm. The abbreviations used below are the following:

s=singlet; m=multiplet; d=doublet; t=triplet; q=quartet.

The phenyl group in the compounds (I) will be conventionally numbered hereinbelow as follows:

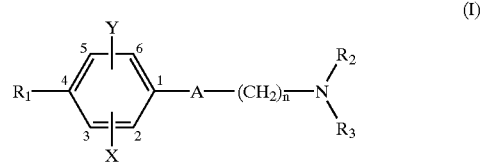

Preparation 1

1-Bromo-4-(1,1-dimethoxyethyl)benzene, Compound Vp (Vp): X=Y=H; Z=Br; P=CH$_3$

A mixture of 19.905 g of 1-(4-bromophenyl)ethanone, 101.4 ml of methanol, 0,22 g of para-toluenesulphonic acid hydrate and 19.9 ml of trimethyl orthoformate is stirred for 6 hours at room temperature. The solution is neutralized with a 1% solution of potassium hydroxide in methanol, and concentrated under reduced pressure. The oil obtained is taken up in petroleum ether, the precipitate is removed by filtration and the filtrate is evaporated under reduced pressure. Compound IVp is purified by distillation; yield=96%; b.p.=82° C. (at a pressure of 0.03 mbar).

Preparation 2

4,4-Dimethylcyclohexanone, Compound 3.1 a) 4,4-Dimethylcyclohex-2-enone 1 ml of concentrated sulphuric acid is added at room temperature to 81 ml of but-3-en-2-one and 88 ml of 2-methylpropionaldehyde in 450 ml of benzene, after which the reaction mixture is refluxed for 13 hours to remove the water by azeotropic entrainment. After cooling to room temperature, the reaction mixture is washed with saturated aqueous sodium bicarbonate solution and then with water. The organic phase is dried over magnesium sulphate and the solvents are evaporated off under reduced pressure. After distillation, 31.1 g of the expected compound are isolated; b.p.=78° C. (at a pressure of 22 mbar).

b) 31.1 g of 4,4-dimethylcyclohex-2-enone in 100 ml of pentane are hydrogenated in an autoclave at a pressure of 5 bar in the presence of 1.6 g of 5% palladium on charcoal. The reaction mixture is filtered and the solvents are evaporated off under reduced pressure.

Preparation 3

4-Bromo-3,5-dichlorophenol, Compound IXa.1 a) N-(3,5-Dichlorophenyl)acetamide 200 ml of pyridine are added dropwise to 100 g of 3,5-dichlorophenylamine in 3000 ml of chloroform, followed by addition of 90 ml of acetic anhydride. The reaction mixture is stirred for 12 hours at room temperature. The solvents are evaporated off under reduced pressure and the residue obtained is recrystallized from 1000 ml of ethyl acetate; m.p.=182° C.

b) N-(4-Bromo-3,5-dichlorophenyl)acetamide 21.3 ml of bromine diluted in 82 ml of acetic acid are added over 6 hours to 84.86 g of N-(3,5-dichlorophenyl) acetamide and 34 g of sodium acetate in 420 ml of acetic acid. After 12 hours at room temperature, the reaction mixture is heated for 5 hours at 50° C. The solvents are evaporated off under reduced pressure. The residue obtained is recrystallized from isopropanol; m.p.=224° C.

c) 4-Bromo-3,5-dichlorophenylamine 202 g of N-(4-bromo-3,5-dichlorophenyl)acetamide and 220 g of sodium hydroxide (as an aqueous 50% solution) in 670 ml of ethylene glycol are stirred for 5 hours at 120° C. and then for 12 hours at room temperature. 3000 ml of water are added, the mixture is filtered, the organic phase is dried over magnesium sulphate and the solvents are evaporated off under reduced pressure. The residue obtained is crystallized from cyclohexane; m.p.=132° C.

d) 100 g of 4-bromo-3,5-dichlorophenylamine are added with stirring at 5° C. to a mixture of 125 ml of water and 90 ml of concentrated sulphuric acid. 230 g of crushed ice are added to the reaction mixture, followed by 29 g of sodium nitrite in 70 ml of water, and the reaction mixture is left stirring for 15 minutes. The reaction mixture is added rapidly to a mixture composed of 280 ml of concentrated sulphuric acid and 200 ml of water raised to 160° C., and the reaction mixture is left stirring at 160° C. for 1 hour. The reaction mixture is poured onto a water/crushed ice mixture and extracted with dichloromethane. The organic phase is dried over magnesium sulphate and the solvents are evaporated off under reduced pressure. The residue obtained is purified by chromatography on a column of silica gel, eluting with a 4/6 (v/v) cyclohexane/dichloromethane mixture.

$^1$H NMR: 10.5 (s, 1H); 7.0 (s, 2H).

Preparation 4

1-[4-(1-Hydroxy-3,3,5,5-tetramethylcyclohexyl) phenyl]ethanone, Compound V'.1

(V'.1):

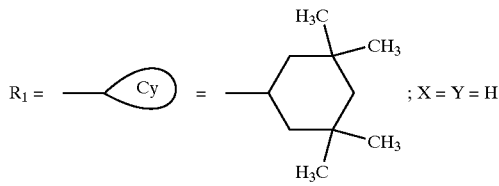

27.5 ml of a 1.6 M solution of n-butyllithium in hexane are added dropwise at −78° C. to a solution of 10 g of 1-bromo-4-(1,1-dimethoxyethyl)benzene (compound Vp) in 100 ml of tetrahydrofuran. The reaction mixture is stirred for 2 hours at this temperature. A solution of 6.92 ml of 3,3,5,5-tetramethylcyclohexanone in 20 ml of tetrahydrofuran is added over 20 minutes and the reaction mixture is stirred at −78° C. for 1 hour. After warming to room temperature, 140 ml of saturated aqueous ammonium chloride solution are added. The phases are separated after settling has taken place, the aqueous phase is extracted with diethyl ether, the organic phases are combined and dried over magnesium sulphate, and the solvents are evaporated off under reduced pressure. The oil obtained is purified by chromatography on a column of silica gel, eluting with a 95/5 (v/v) cyclohexane/ethyl acetate mixture; yield=88%; m.p.=135° C.

The following compounds are prepared in the same way:

1-[4-(Hydroxy-3,3-dimethylcyclohexyl)phenyl] ethanone, Compound V'.2

(V'.2):

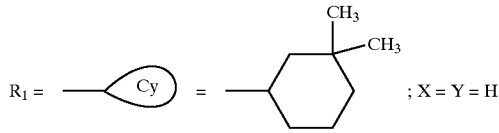

m.p.=99° C.

1-[4-(Hydroxyadamantan-2-yl)phenyl]ethanone, Compound V'.3

(V'.3):

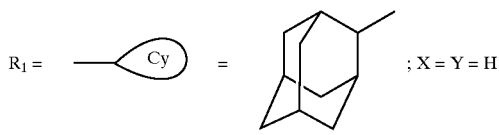

$^1$H NMR: 7.9 (d, 2H); 7.6 (d, 2H); 4.8 (s, 1H); 2.6–1.4 (m, 18H).

1-[4-(Hydroxy-4,4-dimethylcyclohexyl)phenyl]ethanone, Compound V'.4

(V'.4):

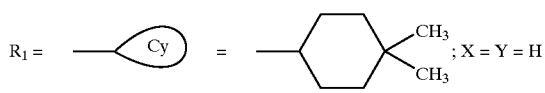

m.p.=88° C.

Preparation 5

1-[4-(3,3,5,5-Tetramethylcyclohexyl)phenyl]ethanone, Compound V.1

(V.1):

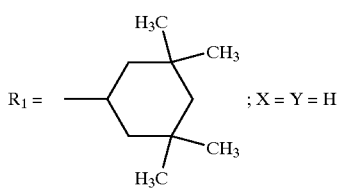

38.1 ml of chlorotrimethylsilane are added over 45 minutes to a solution of 40.45 g of 1-[4-(hydroxy-3,3,5,5-tetramethylcyclohexyl)phenyl]ethanone (compound V'.1) and 56.21 g of sodium iodide in 230 ml of anhydrous acetonitrile. During the addition, the temperature is maintained between 35° C. and 40° C. After stirring for 2 hours, 40 ml of acetonitrile and 39.4 ml of acetic acid are added. Next, 29.4 g of finely powdered zinc are added portionwise with stirring and at room temperature. The mixture is refluxed with vigorous stirring for 4 hours. After cooling to room temperature, the reaction medium is filtered through Celite and then washed with saturated aqueous sodium bicarbonate solution. The organic phase is concentrated under reduced pressure and the oil obtained is purified by chromatography on a column of silica gel, eluting with a 95/5 (v/v) cyclohexane/ethyl acetate mixture; yield=68%; m.p.=54° C.

The following compounds are obtained in the same way:

1-[4-(3,3-Dimethylcyclohexyl)phenyl]ethanone, Compound V.2

(V.2):

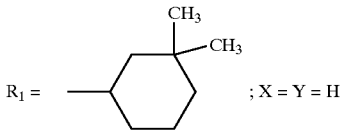

$^1$H NMR: 7.8 (d, 2H); 7.2 (d, 2H); 2.7 (m, 1H); 2.5 (s, 3H); 1.8–1.1 (m, 8H); 1.0 (s, 3H); 0.9 (s, 3H).

1-(4-Adamantan-2-ylphenyl)ethanone, Compound V.3

(V.3):

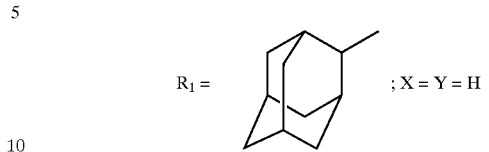

m.p.=75° C.

Preparation 6

1-[4-(4,4-Dimethylcyclohex-1-enyl)phenyl]ethanone, Compound VI.1 a) 1-[4-(1,1-Dimethoxyethyl)phenyl]-4,4-dimethylcyclohexanol 328 ml of a 1.6 M solution of butyllithium in cyclohexane are added at −78° C. to 117 g of 1-bromo-4-(1,1-dimethoxyethyl)benzene in 1100 ml of tetrahydrofuran and the reaction mixture is stirred at −78° C. for 2 hours. 66 g of 4,4-dimethylcyclohexane dissolved in 210 ml of tetrahydrofuran are added at this same temperature and the reaction mixture is stirred for 1 hour at −78° C. The reaction mixture is hydrolysed by addition of crushed ice. The organic phase is separated out after settling of the phases has taken place, it is dried over sodium sulphate and the solvents are evaporated off under reduced pressure. The compound obtained is recrystallized from 500 ml of n-hexane; m.p.=88° C.

b) 99.32 g of 1-[4-(1,1-dimethoxyethyl)phenyl]-4,4-dimethylcyclohexanol in 300 ml of dichloromethane, and 151 g of sodium iodide are added to 600 ml of acetonitrile, under an inert atmosphere, and the reaction mixture is heated to 30° C. 102 ml of chlorotrimethylsilane chloride are added, followed, at 65° C., by portionwise addition of a mixture of 300 ml of acetonitrile and 47 ml of acetic acid, and the reaction mixture is stirred for 12 hours at room temperature. The reaction mixture is filtered and extracted with dichloromethane. The residue obtained is purified by chromatography on a column of silica gel, eluting with a 99/1 (v/v) cyclohexane/ethyl acetate mixture.

Preparation 7

1-[4-(4,4-Dimethylcyclohexyl)phenyl]ethanone, Compound V.4 a) 1-(1,1-Dimethoxyethyl)-4-(4,4-dimethylcyclohex-1-enyl)benzene 36.13 g of 1-[4-(4,4-dimethylcyclohex-1-enyl)phenyl]ethanone (compound VI.1) in 250 ml of methanol are stirred for 12 hours at room temperature in the presence of 0.5 g of para-toluenesulphonic acid (PTSA) and 13 ml of trimethyl-ortho-formate. The solvents are partially evaporated off under reduced pressure. A 50% solution of potassium hydroxide in methanol is added and the solvents are then evaporated off under reduced pressure. The residue obtained is taken up in diisopropyl ether and the solvent is then evaporated off under reduced pressure.

b) the compound obtained in a) in 250 ml of methanol is hydrogenated in the presence of 3 g of 5% palladium on charcoal. The reaction mixture is filtered, the solvents are evaporated off under reduced pressure and the residue obtained is taken up in dichloromethane. The reaction mixture is stirred for 12 hours in the presence of silica and filtered, the solvents are evaporated off under reduced pres- Preparation 8

1-[3-Chloro-4-(3,3,5,5-tetramethylcyclohexyl)phenyl]ethanone, Compound V.5

(V.5):

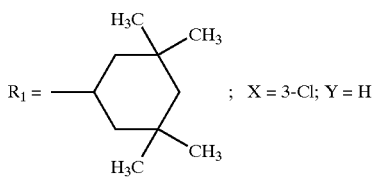

40.25 g of aluminium chloride are added at 0° C., under an inert atmosphere, to 350 ml of dichloromethane, followed by addition of 5 g of 1-[4-(3,3,5,5-tetramethylcyclohexyl)phenyl]ethanone (compound V.1) dissolved in dichloromethane. After stirring for 2 hours at 0° C., 17.1 ml of chlorine gas (d=1.565, measured in the liquid state at −78° C.) are bubbled into the reaction. After warming to room temperature, a water/ice mixture is added to the reaction mixture. The resulting mixture is extracted with dichloromethane, the phases are separated after settling has taken place, and the organic phase is dried over magnesium sulphate and concentrated under reduced pressure. The residue is purified on a column of silica gel, eluting with a 7/3 (v/v) cyclohexane/dichloromethane mixutre; yield=74%; m.p.=64° C.

The following dichloro compounds are also isolated by chromatography:

1-[3,5-Dichloro-4-(3,3,5,5-tetramethylcyclohexyl)phenyl]ethanone, Compound V.6

(V.6):

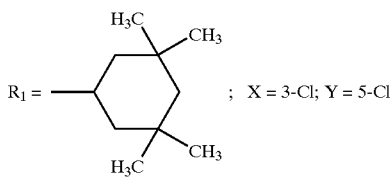

$^1$H NMR: 7.9 (s, 1H); 7.8 (s, 1H); 3.9 (m, 1H); 2.5 (s, 3H); 2.1 (m, 2H); 1.2 (m, 4H); 1.0 (s, 6H); 0.9 (s, 6H).

1-[3,6-Dichloro-4-(3,3,5,5-tetramethylcyclohexyl)phenyl]ethanone, Compound V.7

(V.7):

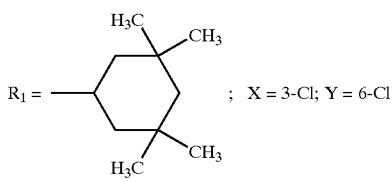

$^1$H NMR: 7.6 (s, 1H); 7.2 (s, 1H); 3.3 (m, 1H); 2.6 (s, 3H); 1.5 (m, 2H); 1.2 (m, 4H); 1.1 (s, 6H); 0.9 (s, 6H).

According to the procedure described for compound V.5, the following compounds are isolated:

1-[3-Chloro-4-(3,3-dimethylcyclohexyl)phenyl]ethanone, Compound V.8

(V.8):

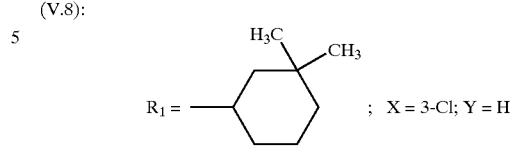

$^1$H NMR: 7.9 (1H, s); 7.8 (d, 1H); 7.4 (d, 1H); 3.1 (m, 1H); 2.5 (s, 3H); 1.8–1.1 (m, 8H); 0.9 (s, 3H); 0.8 (s, 3H).

1-(3-Chloro-4-tert-butylphenyl)ethanone, Compound V.9

(V.9):

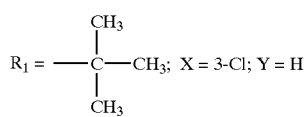

$^1$H NMR: 7.8 (s, 1H); 7.7 (d, 1H); 7.5 (d, 1H); 2.5 (s, 3H); 1.4 (s, 9H).

1-(3,5-Chloro-4-cyclohexylphenyl)ethanone, Compound V.10

(V.10):

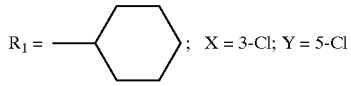

1-[3-Chloro-(4,4-dimethylcyclohexyl)phenyl]ethanone, Compound V.11

(V.11):

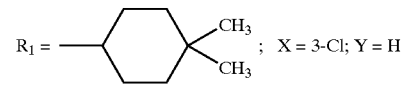

$^1$H NMR: 7.9 (s, 1H); 7.8 (d, 1H); 7.5 (d, 1H); 2.8 (m, 1H); 2.5 (s, 3H); 1.8–1.1 (m, 8H); 0.95 (s, 3H); 0.9 (s, 3H)

Preparation 9

1-[(3-Chloro-4-hydroxy)phenyl]ethanone, Compound VII.1

(VII.1): X=3-Cl; Y=H 167 g of aluminium trichloride are added, under an inert atmosphere, to 63.5 ml of 2-chloro-1-methoxybenzene in 500 ml of 1,2-dichloroethane, followed by dropwise addition of 167 g of acetyl chloride dissolved in 200 ml of 1,2-dichloroethane. The reaction mixture is heated at 45° C. for 48 hours. The reaction mixture is poured onto a water/ice mixture and extracted with dichloromethane, the solvents are evaporated off under reduced pressure and the residue obtained is purified by chromatography on a column of silica gel, eluting with a 90/10 (v/v) cyclohexane/ethyl acetate mixture. Compound VII.1 is recrystallized from cyclohexane; m.p.=107° C.

Preparation 10

Cyclohexylethylprop-2-ynylamine, Compound (4.1)

20 ml of 80% 3-bromopropyne are added dropwise to 30.3 ml of cyclohexylethylamine and 29.7 g of potassium carbonate in 300 ml of acetonitrile. The reaction mixture is heated at 50° C. for 12 hours and at 80° C. for 6 hours. The resulting mixture is filtered and the solvents are evaporated off under reduced pressure. Compound V.1 is purified by distillation.

$^1$H NMR: 3.3 (s, 2H); 3.0 (s, 1H); 2.5 (q, 2H); 2.4 (m, 1H); 1.8–1.1 (m, 10H); 1.0 (t, 3H).

The following compounds are prepared in the same way:

Cyclohexylmethylprop-2-ynylamine, Compound 4.2

Cyclohexylisopropylprop-2-ynylamine, Compound 4.3

Preparation 11

Cyclohexylethylbut-3-ynylamine, Compound (4.4)

a) But-3-yne(4-methylphenyl) sulphonate 74.8 g of tosyl chloride are added to 36 ml of pyridine at 80° C. The reaction mixture is cooled to 15° C. and 25 g of but-3-yn-1-ol are then added. The reaction mixture is stirred at room temperature for 12 hours, 70 ml of water are then added at 15° C., the resulting mixture is extracted with diethyl ether and the organic phase is then washed with dilute aqueous sulphuric acid solution and then with saturated aqueous sodium hydrogen carbonate solution. The organic phase is dried over sodium sulphate and the solvents are evaporated off under reduced pressure.

$^1$H NMR: 7.8 (d, 2H); 7.4 (d, 2H); 4.0 (t, 2H); 3.8 (s, 1H); 2.5 (t, 2H); 2.4 (s, 3H)

b) 57.9 g of the compound obtained in a), 21.7 g of sodium hydrogen carbonate and 35.7 ml of cyclohexylethylamine in 100 ml of dimethylformamide are refluxed for 12 hours. The reaction mixture is poured into water and extracted with diethyl ether. The organic phase is dried over magnesium sulphate and the solvents are evaporated off under reduced pressure. After distillation, the expected amine is isolated; b.p.=92–94° C. (at a pressure of 13 mbar).

Preparation 12

4-Acetyl-2-chlorophenyl Trifluoromethanesulphonate, Compound Va.1

(Va.1): X=3-Cl; Y=H; Z=OTf 26.2 ml of triflic anhydride are added dropwise at 0° C. to 26.7 g of 1-[(3-chloro-4-hydroxy)phenyl]ethanone (compound VII.1) in 700 ml of pyridine. The reaction mixture is stirred at 0° C. for 36 hours, the solvents are evaporated off under reduced pressure and the residue is taken up in a 0.1 N solution of hydrochloric acid in dichloromethane. The phases are separated after settling has taken place, the organic phases are dried over magnesium sulphate and the solvents are evaporated off under reduced pressure. The residue obtained is purified by chromatography on a column of silica gel, eluting with a 95/5 (v/v) cyclohexane/ethyl acetate mixture.

$^1$H NMR: 8.2 (s, 1H); 8.0 (d, 1H); 7.8 (d, 1H).

The following compounds are prepared in the same way:

4-Acetyl-2,6-dichlorophenyl Trifluoromethanesulphonate, Compound Va.2

(Va.2): X=3-Cl; Y=6-Cl; Z=OTf $^1$H NMR: 8.2 (s, 2H); 2.6 (s, 3H).

4-Bromo-2-chlorophenyl Trifluoromethanesulphonate, Compound IIIa.1 starting with 4-bromo-2-chlorophenol.

(IIIa.1): X=3-Cl; Y=H $^1$H NMR: 8.1 (s, 1H); 7.7 (d, 1H); 7.6 (d, 1H).

Preparation 13

2-Chloro-4-[3-(cyclohexylethylamino)prop-1-ynyl] phenyl Trifluoromethane-sulphonate, Compound Ia.1

(Ia. 1): Z=OTf; X=3-Cl; Y=H;

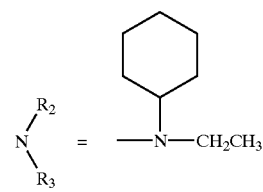

2.14 g of cyclohexylethylprop-2-ynylamine (compound VII.1) are added, under inert atmosphere, to 4 g of 4-bromo-3-chlorophenyl trifluoromethanesulphonate (compound IIIa.1), 0.06 g of copper iodide, 10 ml of pyridine and 20 ml of triethylamine, followed by addition of 0.413 g of the catalyst dichlorobis(triphenylphosphine)palladium VI. The reaction mixture is refluxed for 2 hours and then left at room temperature for 12 hours. The resulting mixture is filtered and the solvents are evaporated off under reduced pressure. The residue is purified by chromatography on a column of silica gel, eluting with a dichloromethane/ethanol mixture varying from 100/0 to 99/1 (v/v). The compound obtained is taken up in dichloromethane and filtered, and the solvents are evaporated off under reduced pressure; yield=76%

$^1$H NMR: 7.8 (s, 1H); 7.6 (d, 1H); 7.5 (d, 1H); 3.6 (s, 2H); 2.6 (q, 2H); 2.4 (m, 1H); 1.9–1.1 (m, 10H); 0.9 (t, 3H).

Preparation 14

1-[3-Chloro-4-(4-fluorophenyl)phenyl]ethanone, Compound V.12

(V.12):

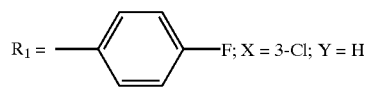

19.7 g of 4-acetyl-2-chlorophenyl trifluoromethanesulphonate (compound X.1), 10 g of 4-fluorobenzeneboronic acid, 2 g of tetrakis (triphenylphosphine)palladium, 17.9 g of sodium carbonate in 84.5 ml of water, 591 ml of toluene, 200 ml of ethanol and 5.51 g of lithium chloride are stirred under an inert atmosphere at 60° C. for 8 hours. The reaction mixture is then stirred for 12 hours at room temperature. The resulting mixture is filtered and the solvents are evaporated from the filtrate under reduced pressure. The residue obtained is purified by chromatography on a column of silica gel, eluting with a 97/3 (v/v) cyclohexane/ethyl acetate mixture; yield=94%.

$^1$H NMR: 8.0 (s, 1H); 7.9 (d, 1H); 7.5 (m, 3H); 7.3 (m, 2H); 2.6 (s, 3H).

The compounds V.13 to V.17 given in TABLE 1 below are prepared in the same way:

TABLE 1

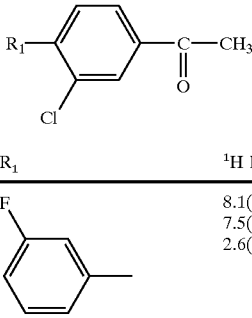

(V)

| COMPOUND | R₁ | ¹H NMR |
|---|---|---|
| V.13 | 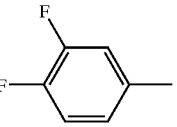 | 8.1(s, 1H); 7.9(d, 1H); 7.5(m, 2H); 7.2(m, 3H); 2.6(s, 3H) |
| V.14 | 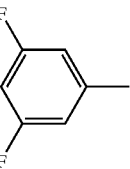 | 8.0(s, 1H); 7.9(d, 1H); 7.6(m, 3H); 7.3(m, 1H); 2.6(s, 3H) |
| V.15 | 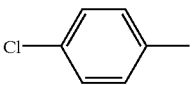 | 8.0(s, 1H); 7.9(d, 1H); 7.6(d, 1H); 7.4–7.1(m, 3H) 2.6(s, 3H) |
| V.16 | 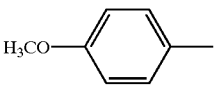 | 8.0(s, 1H); 7.9(d, 1H); 7.5(m, 5H); 2.6(s, 3H) |
| V.17 | 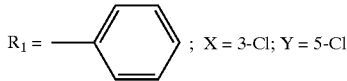 | 8.0(s, 1H); 7.9(d, 1H); 7.5(d, 1H); 7.4(m, 2H); 7.0(m, 2H); 3.8(s, 3H); 2.6(s, 3H) |

1-(2,6-Dichlorobiphenyl-4-yl)ethanone, Compound V.18

(V.18):

R₁ = 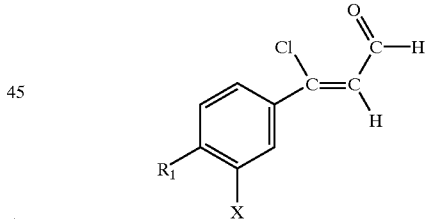 ; X = 3-Cl; Y = 5-Cl

¹H NMR: 8.0 (s, 2H); 7.4 (m, 3H); 7.2 (m, 2H); 2.6 (s, 3H).

1-(2,6-Dichloro-4'-fluorobiphenyl-4-yl)ethanone, Compound V.19

(V.19):

R₁ = 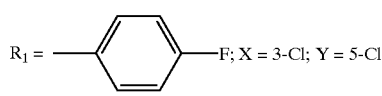 F; X = 3-Cl; Y = 5-Cl

¹H NMR: 8.0 (s, 2H); 7.3 (m, 4H); 2,6 (s, 3H).

Preparation 15

3-Chloro-3-[3-chloro-4-(3,3,5,5-tetramethylcyclohexyl)phenyl]propenal, Compound IV.1

(IV.1)

R₁ = 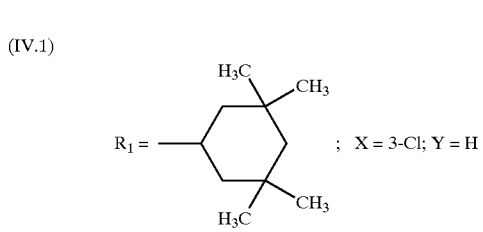 ; X = 3-Cl; Y = H 3.51 ml of oxalyl chloride are added dropwise at a temperature of between –5° C. and 2° C. to a solution of 3.72 ml of dimethylformamide and 20 ml of anhydrous dichloromethane and the reaction mixture is then stirred at room temperature for 30 minutes. 3.92 g of 1-[3-chloro-4-(3,3,5,5-tetramethylcyclohexyl)phenyl]ethanone (compound V.6) dissolved in 10 ml of dichloromethane are then added rapidly, after which the reaction mixture is stirred at room temperature for 12 hours. The reaction mixture is poured into a water/ice mixture and 20 ml of aqueous 2.84 M sodium ethoxide solution are then added. The resulting mixture is washed with 50 ml of sodium hydrogen carbonate solution and 50 ml of water, the phases are separated after settling has taken place, the organic phase is dried over magnesium sulphate and the solvents are evaporated off under reduced pressure. The oil obtained is purified by chromatography on a column of silica gel, eluting with a 97/3 (v/v) cyclohexane/ethyl acetate mixture.

¹H NMR: 10.2 (d, 1H); 7.7 (s, 1H); 7.5 (d, 1H); 7.3 (d, 1H); 6.6 (d, 1H); 3.4 (m, 1H); 1.5 (m, 2H); 1.3 (m, 4H); 1.1 (s, 6H); 0.9 (s, 6H).

Compounds IV.2 to IV.17 given in TABLES 2 and 3 below are prepared in the same way:

TABLE 2

(IV)

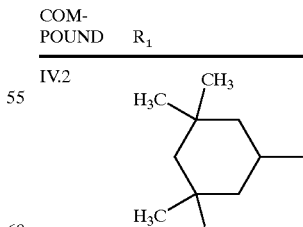

in which Y = H

| COMPOUND | R₁ | X | m.p.; °C. or ¹H NMR |
|---|---|---|---|
| IV.2 | 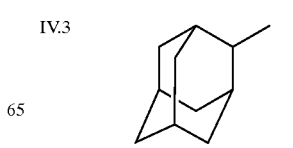 | H | 10.1(d, 1H); 7.8(m, 2H); 7.4(m, 2H); 6.9(m, 1H); 2.9(m, 1H); 1.4–0.8(18H) |
| IV.3 |  | H | 146 |

TABLE 2-continued (IV)

Structure: Aryl group (with R1 and X substituents) connected to C(Cl)=CH-CHO in which Y = H

| COMPOUND | R₁ | X | m.p.; °C. or ¹H NMR |
|---|---|---|---|
| IV.4 | 4-F-phenyl | H | |
| IV.5 | 3-F-phenyl | H | |
| IV.6 | 1,3-dimethylcyclohexyl (1-CH₃, 3-CH₃) | Cl | 10.0(d, 1H); 7.8(s, 1H); 7.7(d, 1H); 7.4(d, 1H); 7.0(d, 1H); 3.1(m, 1H); 1.8–1.1(m, 8H); 1.0(s, 3H); 0.9(s, 3H) |
| IV.7 | tert-butyl (C(CH₃)₃) | Cl | |
| IV.8 | 4-F-phenyl | Cl | 139 |
| IV.9 | 3-F-phenyl | Cl | |
| IV.10 | 3,4-difluorophenyl | Cl | |
| IV.11 | 3,5-difluorophenyl | Cl | |
| IV.12 | 4-Cl-phenyl | Cl | |
| IV.13 | 4-methoxyphenyl (H₃CO-) | Cl | 10.1(d, 1H); 8.0(s, 1H); 7.9(d, 1H); 7.6–7.3(m, 3H); 7.1(m, 2H); 7.0 (d, 1H); 3.8(s, 3H) |
| IV.14 | 1,1-dimethylcyclohexyl ((H₃C)₂C-) | Cl | 10(d, 1H); 7.9(s, 1H); 7.8(d, 1H); 7.5(d, 1H); 7.0(d, 1H); 4.8(m, 1H); 1.7–1.1(m, 8H); 0.95(s, 3H); 0.9(s, 3H) |

TABLE 3

(IV)

Structure: Aryl group (with R₁ and Y substituents) connected to C(Cl)=CH-CHO, with Cl on ring in which X = Cl

| COMPOUND | R₁ | Y | m.p.; °C. or ¹H NMR |
|---|---|---|---|
| IV.15 | 1,1,3,3-tetramethylcyclohexyl | 5-Cl | 10.1(d, 1H); 8.0(s, 1H); 7.9(s, 1H); 7.1(d, 1H); 3.9(m, 1H); 2.1(m, 2H); 1.3(m, 4H); 1.1(s, 6H); 0.9(s, 6H) |
| IV.16 | 1,1,3,3-tetramethylcyclohexyl | 6-Cl | 10.0(d, 1H); 7.8–7.4(m, 2H); 6.6(d, 1H); 3.2(m, 1H); 1.6–1.2(m, 6H); 1.0(s, 6H); 0.9(s, 6H) |
| IV.17 | phenyl | 5-Cl | 108 |

Preparation 16

3-Chloro-4-(3,3,5,5-tetramethylcyclohexyl)phenylethyne, Compound II.1.

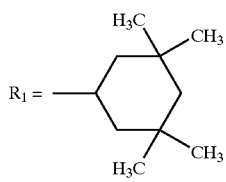

$R_1 =$ (3,3,5,5-tetramethylcyclohexyl); X = 3-Cl; Y = H     (II.1)

5.3 g of sodium hydroxide are dissolved in 150 ml of water under an inert atmosphere and with vigorous stirring. 80 ml of 1,4-dioxane are added and the mixture is heated to reflux. 15 g of 3-chloro-3-[3-chloro-4-(3,3,5,5-tetramethylcyclohexyl)phenyl]propenal (compound IV.1) dissolved in 130 ml of 1,4-dioxane are added rapidly and the reaction mixture is maintained at reflux for 1 hour. After cooling to room temperature, the reaction mixture is poured into a large volume of dichloromethane. The phases are separated after settling has taken place, the organic phase is dried over magnesium sulphate and the solvents are evaporated off under reduced pressure. The residue is purified by chromatography on a column of silica gel, eluting with cyclohexane; yield=80%.

$^1$H NMR: 7.5 (s, 1H); 7.3 (m, 2H); 4.2 (s, 1H); 3.2 (m, 1H); 1.4 (m, 2H); 1.2 (m, 4H); 1.0 (s, 6H); 0.9 (s, 6H).

Compounds II.2 to II.15 given in TABLES 4 and 5 below are prepared in the same way:

TABLE 4

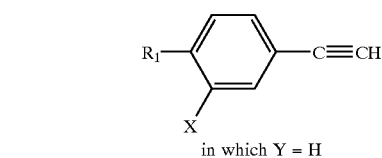
(II)

in which Y = H

| COMPOUND | $R_1$ | X | m.p.; °C. or $^1$H NMR |
|---|---|---|---|
| II.2 | 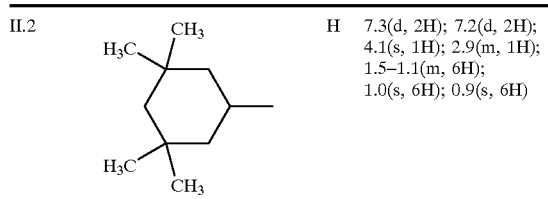 | H | 7.3(d, 2H); 7.2(d, 2H); 4.1(s, 1H); 2.9(m, 1H); 1.5–1.1(m, 6H); 1.0(s, 6H); 0.9(s, 6H) |
| II.3 | 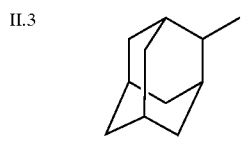 | H | |

TABLE 4-continued

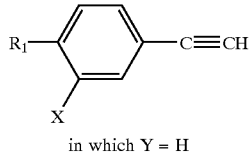
(II)

in which Y = H

| COMPOUND | $R_1$ | X | m.p.; °C. or $^1$H NMR |
|---|---|---|---|
| II.4 | 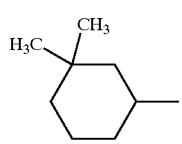 | Cl | 7.4(s, 1H); 7.3(d, 1H); 7.2(d, 1H); 4.0(s, 1H); 3.0(m, 1H); 1.7–1.0(m, 8H); 0.9(s, 3H); 0.8(s, 3H) |
| II.5 | 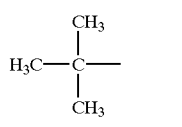 | Cl | 7.4(m, 3H); 4.2 (s, 1H); 1.3(s, 9H) |
| II.6 | 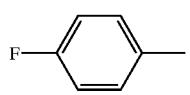 | Cl | 7.6(s, 1H); 7.4 (m, 6H); 4.3(s, 1H) |
| II.7 | 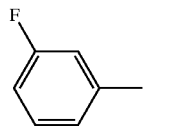 | Cl | 7.7(s, 1H); 7.5 (m, 3H); 7.3(m, 3H); 4.3 (s, 1H) |
| II.8 | 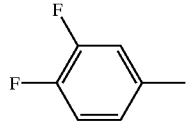 | Cl | 7.7(s, 1H); 7.5 (m, 4H); 7.3(m, 1H); 4.3 (s, 1H) |
| II.9 | 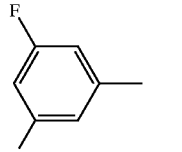 | Cl | |
| II.10 | 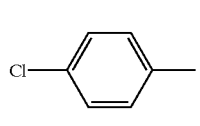 | Cl | 78 |
| II.11 | 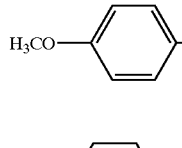 | Cl | 7.6(s, 1H); 7.4(d, 1H); 7.3(m, 3H); 7.0 (d, 2H); 4.3(s, 1H); 3.8 (s, 3H) |
| II.12 | 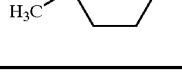 | Cl | 7.5(s, 1H); 7.4(m, 2H); 4.2(s, 1H); 2.8(m, 1H); 1.7–1.2(m, 8H); 0.95(s, 3H); 0.9 (s, 3H) |

TABLE 5

(II)

$$R_1 \underset{Cl}{\underset{|}{\diagdown}} \overset{Y}{\underset{|}{\diagup}} - C \equiv CH$$

in which X = Cl

| COMPOUND | R₁ | Y | m.p.; °C. or ¹H NMR |
|---|---|---|---|
| II.13 | H₃C—C(CH₃)—CH₂—C(CH₃)(H₃C)—cyclohexyl | 5-Cl | 7.6(s, 1H); 7.5(s, 1H); 4.4(s, 1H); 3.9(m, 1H); 2.0(t, 2H); 1.2(m, 4H); 1.1(s, 6H); 0.9(s, 6H) |
| II.14 | H₃C—C(CH₃)—CH—C(CH₃)(H₃C)—cyclohexyl | 6-Cl | 7.6(s, 1H); 7.4(s, 1H); 4.6(s, 1H); 3.2(m, 1H); 1.5–1.1(m, 6H); 1.0(s, 6H); 0.9(s, 6H) |
| II.15 | phenyl | 5-Cl | 7.7(s, 2H); 7.4 (m, 3H); 7.2(d, 2H); 4.5 (s, 1H) |

Preparation 17

3,5-Difluorobenzeneboronic Acid, Compound 2.1

91.5 ml of tert-butyllithium are added at −78° C. to 20 g of 1-bromo-3,5-difluorobenzene in 300 ml of diethyl ether. The reaction mixture is stirred for 1 hour at −78° C. and 14.2 ml of trimethyl borate are then added. The reaction mixture is stirred for 1 hour at −78° C. and then for 12 hours at room temperature. 200 ml of aqueous 1 N hydrochloric acid solution are added. The resulting mixture is extracted with diethyl ether, the organic phase is washed with saturated sodium hydrogen carbonate solution and dried over magnesium sulphate, and the solvents are evaporated off under reduced pressure. The residue is taken up in cyclohexane and the precipitate obtained is isolated by filtration.

¹H NMR:7.4 (m, 3H); 7.2 (m, 2H).

Preparation 18

4-Bromo-3-chloroacetophenone, Compound Va. 3

(Va.3); X=3-Cl; Y=H ; Z=Br

A solution of 100 g of 4-bromoacetophenone in 250 ml of dichloromethane is added dropwise at 0° C. to 133.34 g of aluminium chloride in 600 ml of dichloromethane. After stirring for 2 hours at 0° C., 28.3 ml of prefrozen (−75° C.) chlorine are bubbled into the medium at 0° C. The reaction mixture is stirred at room temperature for 12 hours and then hydrolysed. The phases are separated after settling has taken place, the aqueous phase is extracted with dichloromethane, the organic phases are dried over magnesium sulphate and the solvents are evaporated off under reduced pressure. The residue obtained is recrystallized from hexane; yield=57%; m.p.=80° C.

Preparation 19

3-Chloro-3-(4-bromo-3-chlorophenyl)propenal, Compound IVa. 1

(IVa.1): X=3-Cl; Y=H ; Z=Br 15.08 ml of oxalyl chloride are added at a temperature of between 3° C. and 6° C. with vigorous stirring to 16 ml of dimethylformamide in 200 ml of dichloromethane. After warming to room temperature, the mixture is stirred for 30 minutes, followed by addition of a solution of 13.4 g of 4-bromo-3-chloroacetophenone (compound Va.3) in 40 ml of dichloromethane. The reaction mixture is stirred for 12 hours at room temperature and then hydrolysed by addition of a solution of 18.9 g of sodium acetate in 50 ml of water. After stirring for 30 minutes at room temperature, the phases are separated after settling has taken place, the aqueous phase is extracted with dichloromethane, the organic phases are dried over magnesium sulphate and the solvents are evaporated off under reduced pressure. The residue obtained is recrystallized from cyclohexane; yield=87%; m.p=134° C.

Preparation 20

[3-(4-Bromo-3-chlorophenyl)prop-2-ynyl] cyclohexylethylamine, Compound Ia.2

(Ia.2): X=3-Cl; Y=H; Z=Br;

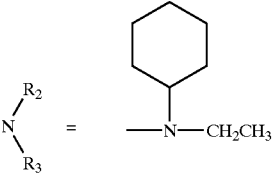

a) 1-Bromo-2-chloro-4-ethynylbenzene 40 g of sodium hydroxide are dissolved, under an inert atmosphere, in 230 ml of water, 120 ml of 1,4-dioxane are added and the reaction mixture is heated to 80° C. 17.5 g of 3-chloro-3-(4-bromo-3-chlorophenyl)propenal dissolved in 400 ml of 1,4-dioxane are added and the reaction mixture is stirred for 30 minutes at 80° C. The reaction mixture is allowed to cool to room temperature and 2300 ml of dichloromethane are then added. The phases are separated after settling has taken place and the organic phase is washed with water and dried over magnesium sulphate. The compound dissolved in a dichloromethane/1,4-dioxane mixture is used in its current form in the next step.

b) [3-(4-Bromo-3-chlorophenyl)prop-2-ynyl] cyclohexylethylamine.

Aqueous 36% formaldehyde solution is added to 10.36 ml of ethylcyclohexylamine in 400 ml of 1,2-dimethoxyethane. This solution is added to the solution of the compound obtained above in the presence of 0.54 g of copper II chloride dihydrate. The reaction mixture is stirred for 4 hours at reflux and is then left to cool to room temperature. The resulting mixture is filtered, the solvents are evaporated off under reduced pressure and the residue obtained is then purified by chromatography on a column of silica gel, eluting with a 99/1 (v/v) dichloromethane/ethanol mixture. The compound obtained is taken up in diethyl ether and hydrogen chloride is bubbled through. The precipitate obtained is filtered off and dried to given the compound in the form of the hydrochloride. ¹H NMR: 7.7 (d, 1H); 7.6 (s, 1H); 7.2 (d, 1H); 3.5 (s, 2H); 2.6 (q, 2H); 2.4 (m, 1H); 1.8–1.1 (m, 10H); 0.9 (t, 3H).

Preparation 21

2-Chloro-4-(4,4-dimethylcyclohexyl)phenol, Compound IX.1 a) 2-Chloro-4-(1-hydroxy-4,4-dimethylcyclohexyl) phenol 100 ml of a 1.6 M solution of n-butyllithium in hexane are added at −78° C. to 15.1 g of 4-bromo-2-chlorophenol in 150 ml of tetrahydrofuran, and the reaction mixture is stirred at −78° C. for 1 hour. 10.1 g of 4,4-dimethylcyclohexanone (compound 3.1) are added and the reaction mixture is stirred at −78° C. for a further 30 minutes and then at room temperature for 12 hours. The reaction mixture is hydrolysed with 1 N hydrochloric acid solution and extracted with ethyl acetate. The organic phase is dried over magnesium sulphate and the solvents are evaporated off under reduced pressure. The solid obtained is purified by chromatography on a column of silica gel, eluting with a cyclohexane/ethyl acetate mixture varying from 98/2 to 90/10 (v/v). 11.8 g of solid are obtained.

$^1$H NMR: 7.4(s, 1H); 7.2(d, 2H); 6.9(d, 2H); 4.5 (s, 1H); 1.9–1.1 (m, 8H); 0.9 (s, 6H).

b) 50 l of aqueous 57% hydriodic acid solution are added to 11.8 g of 2-chloro-4-(1-hydroxy-4,4-dimethylcyclohexyl) phenol in 200 ml of acetic acid. The reaction mixture is refluxed for 3 hours and the solvents are evaporated off under reduced pressure. Aqueous 40% sodium hydroxide solution, aqueous sodium carbonate solution and then aqueous sodium hydrogen sulphate solution are added and the resulting mixture is extracted with diethyl ether. The organic phase is dried over magnesium sulphate and the solvents are evaporated off under reduced pressure. The compound obtained is purified by chromatography on a column of silica gel, eluting with a 95/5 (v/v) cyclohexane/ethyl acetate mixture.

$^1$H NMR: 9.8 (s, 1H); 7.1 (s, 1H); 7 (d, 1H); 6,9 (d, 1H); 1.9 (m, 1H); 1.6–1.2 (m, 8H); 0.9 (s, 6H)

Compounds IX.2 to IX.4 are prepared according to the same procedure:

4-(Adamantan-2-yl)-3,5-dichlorophenol, Compound IX.2 obtained from compound IXa.1 and adamantan-2-one $^1$H NMR: 10.1 (s, 1H); 6.8 (s, 2H); 3.4 (s, 1H); 2.4 (s, 2H); 2.3–1.4 (m, 12H)

4-(Adamantan-2-yl)phenol, Compound IX.3

$^1$H NMR: 9.1 (s, 1H); 7.1 (d, 2H); 6.7 (d, 2H); 2.8 (s, 1H); 2.4 (s, 2H); 1.9–1.4 (m, 12H)

4-(Adamantan-2-yl)-3-chlorophenol, Compound IX.4

$^1$H NMR: 9.8 (s, 1H); 7.1 (s, 1H); 7.0 (d, 1H); 6.9 (d, 1H); 2.8 (s, 1H); 2.3 (m, 2H); 1.9 (m, 5H); 1.7 (m, 5H); 1.5 (m, 2H)

Preparation 22

4-(Tetrahydropyran-4-yl)phenol, Compound IX.5 a) 4-(3,6-Dihydropyran-4-yl)phenol

[lacuna] is added at −40° C. to 12.7 g of 4-bromophenol in 150 ml of tetrahydrofuran. At this same temperature, 100 ml of 1.6 M butyllithium in hexane are added to the reaction mixture, followed by addition of 8.1 g of 4-tetrahydropyranone. The reaction mixture is left stirring for 18 hours at room temperature and then hydrolysed with 1 N hydrochloric acid. The resulting mixture is extracted several times with diethyl ether, the organic phase is dried over magnesium sulphate and the solvents are evaporated off under reduced pressure. The solid obtained is purified by chromatography on a column of silica gel, eluting with a cyclohexane/ethyl acetate mixture varying from 90/10 to 80/20 (v/v).

$^1$H NMR: 9.4 (s, 1H); 7.2 (d, 1H); 6.7 (d, 1H); 6.0 (t, 1H); 4.1 (d, 2H); 3.7 (t, 2H); 2.4 (t, 2H)

b) 5.5. g of 4-(3,6-dihydropyran-4-yl)phenol are hydrogenated in the presence of 550 mg of 10% palladium on charcoal in 100 ml of methanol, for 3 hours. The mixture is filtered and the solvents are then evaporated off under reduced pressure.

$^1$H NMR: 9.1 (s, 1H); 7 (d, 2H); 6.6 (d, 2H); 3.9 (m, 2H); 3.4 (m, 2H); 2.6 (m, 1H); 1.6 (m, 4H)

The following compound is prepared in the same way:

4-(4,4-Dimethylcyclohexyl)phenol, Compound IX.6

$^1$H NMR: 9 (s, 1H); 7 (d ,2H); 6.7 (d, 2H); 2.2 (m, 1H); 1.6–1.2 (m, 8H); 0.9 (s, 6H)

Preparation 23

4-(Adamantan-2-yl)-3,5-difuorophenol, Compound IX.7 a) 2-(2,6-difluoro-4-methoxyphenyl)adamantan-2-ol

Obtained from 4-bromo-3,5-difluorophenyl methyl ether in the presence of one equivalent of n-butyllithium according to the procedure described in Preparation 22 a).

b) 19 g of the product obtained in the above step, 200 ml of hydroiodic acid and 200 ml of acetic acid are stirred overnight at the reflux temperature. After cooling to room temperature, the reaction mixture is poured into a crushed ice/NaHSO$_3$ mixture. After neutralization with 1 N sodium hydroxide solution, the resulting mixture is extracted with dichloromethane. The organic phase is dried over magnesium sulphate and the solvents are then evaporated off under reduced pressure.

Preparation 24

2-Chloro-4-(4,4-dimethylcyclohexyl)phenyl Trifluoromethanesulphonate, Compound III.1

8.2 ml of triflic anhydride are added at 5° C. to 9.7 g of 2-chloro-4-(4,4-dimethylcyclohexyl)phenol (compound IX.1) in 60 ml of pyridine, and the reaction mixture is left at 0° C. for 30 mintues and then stirred at room temperature for 12 hours. The reaction mixture is hydrolysed and then extracted with dichloromethane. The organic phase is dried over magnesium sulphate and the solvents are evaporated off under reduced pressure. The residue obtained is taken up in toluene and the solvents are then evaporated off under reduced pressure. The residue obtained is purified by chromatography on a column of silica gel, eluting with a cyclohexane/ethyl acetate mixture varying from 100/0 to 99/1 (v/v). 15 g of the compound are obtained.

$^1$H NMR: 7.7 (s, 1H); 7.5 (d, 1H); 7.4 (d, 1H); 2.5 (m, 1H); 1.6–1.2 (m, 8H); 0.92 (s, 3H); 0.86 (s, 3H).

Compounds III.2 to III.7 are prepared according to the same procedure:

4-(Adamantan-2-yl)-3,5-dichlorophenyl
Trifluoromethanesulphonate, Compound III.2

$^1$H NMR: 7.7 (d, 1H); 7.6 (d, 1H); 3.6 (m, 1H); 3.0–1.0 (m, 14H)

4-(Adamantan-2-yl)phenyl
Trifluoromethanesulphonate, Compound III.3

$^1$H NMR: 7.5 (d, 2H); 7.4 (d, 2H); 3.0 (s, 1H); 2.4 (s, 2H); 1.9 (m, 5H); 1.8–1.5 (m, 7H)

4-(Adamantan-2-yl)-3-chlorophenyl
Trifluoromethanesulphonate, Compound III.4

$^1$H NMR: 7.6–7.4 (m, 3H); 3.0 (s, 1H); 2.4 (m, 2H); 1.9 (m, 5H); 1.8–1.4 (m, 7H)

4-(Adamantan-1-yl)phenyl
Trifluoromethanesulphonate, Compound III.5

$^1$H NMR: 7.5 (d, 2H); 7.3 (d, 2H); 2.1 (m, 3H); 1.8 (m, 6H); 1.7 (m, 6H)

4-(Tetrahydropyran-4-yl)phenyl
Trifluoromethanesulphonate, Compound III.6

$^1$H NMR: 7.4 (s, 4H); 3.9 (m, 2H); 3.4 (m, 2H); 2.8 (m, 1H); 1.7 (m, 4H)

4-(4,4-Dimethylcyclohexyl)phenyl
Trifluoromethanesulphonate, Compound III.7

$^1$H NMR: 7.4–7.3 (m, 4H); 2.6 (m, 1H); 1.6–1.2 (m, 8H); 0.93 (s, 3H); 0.90 (s, 3H)

The compounds of the EXAMPLES below are, except where otherwise mentioned, of formula (I) in which:

$n = 1$ and —NR$_2$R$_3$ = 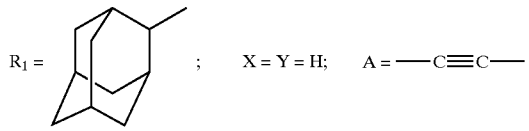

EXAMPLE 1

[3-(4-Adamantan-2-ylphenyl)prop-2-ynyl]cyclohexylethylamine Hydrochloride (I)

$R_1 =$ 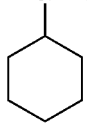 ; $X = Y = H$; $A = \!\!-\!\!\!-\!\!C\!\!\equiv\!\!C\!\!-\!\!\!-$ 8.6 ml of 36% formaldehyde are added to 11.2 ml of cyclohexylethylamine in 100 ml of 1,2-dimethoxyethane and stirring is continued at room temperature for 2 hours. This solution is added to a mixture of 16 g of 2-(4-ethynylphenyl)adamantane (compound II.3) and 0.58 g of copper II chloride dihydrate in 400 ml of 1,2-dimethoxyethane. The reaction mixture is refluxed for 2 hours and the solvents are then evaporated off under reduced pressure. The compound obtained is taken up in diethyl ether, hydrogen chloride is bubbled through and the precipitate obtained is filtered off and dried; m.p.=124° C. (HCl.0.5 H$_2$O).

The compounds of EXAMPLES 2 to 12 given below are prepared in the same way.

EXAMPLE 2

{3-[4-(3,3,5,5-Tetramethylcyclohexyl)phenyl]prop-2-ynyl}cyclohexylethylamine Hydrochloride (I)

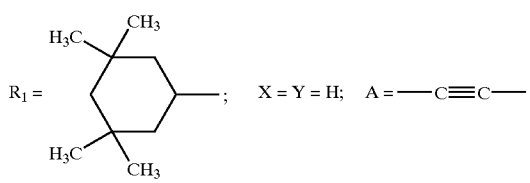

m.p.=150° C. (HCl.0.1 H$_2$O)

TABLE 6

(I)

![structure]

| EXAMPLE | R$_1$ | m.p.; ° C. (salt, hydrate) |
|---|---|---|
| 3 | H$_3$C, CH$_3$ / H$_3$C, CH$_3$ (tetramethylcyclohexyl) | 99 HCl |
| 4 | H$_3$C, CH$_3$ (dimethylcyclohexyl) | 137 HCl |
| 5 | H$_3$C—C(CH$_3$)$_2$—CH$_3$ (tert-butyl) | 156 HCl 0.1 H$_2$O |
| 6 | F—phenyl (4-F) | 148 HCl 0.2 H$_2$O |
| 7 | F—phenyl (3-F) | 130 HCl 0.2 H$_2$O |

TABLE 6-continued

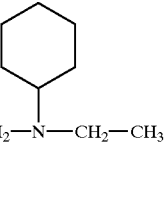

| EXAMPLE | R₁ | m.p.; ° C. (salt, hydrate) |
|---|---|---|
| 8 |  | 0.96(t, 3H); 1.2–1.8(m, 11H); 2.6(q, 2H); 3.6(s, 1H) 7.1–7.4(m, 5H); 7.6(s, 1H) |
| 9 | 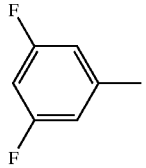 | 172 HCl |
| 10 | 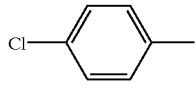 | 50 (pasty) HCl 0.7 H₂O |
| 11 | 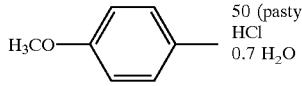 | (a) HCl |

(a) ¹H NMR: 7.4(m, 2H); 7.3(d, 1H); 3.6(s, 2H); 3.4(m, 1H); 2.8(m, 1H); 2.6(q, 2H); 1.3–0.9(m, 27H)

EXAMPLE 12

[3-(2,6-Dichlorobiphenyl-4-yl)prop-2-ynyl] cyclohexylethylamine Hydrochloride

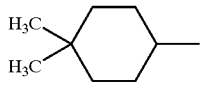

m.p.=205° C. (HCl).

EXAMPLE 13

Compound identical to that of EXAMPLE 7, but prepared in a different manner.

3-(2-Chloro-3'-fluorobiphenyl-4-yl)prop-2-ynyl] cyclohexylethylamine Hydrochloride

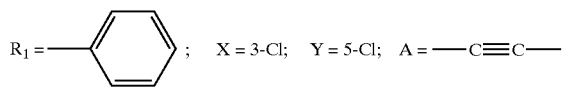

3.4 g of 2-chloro-4-[3-(cyclohexylethylamino)prop-1-ynyl]phenyl trifluoromethanesulphonate (compound Ia.1), 1.23 g of 3-fluorobenzeneboronic acid, 2.2 g of sodium carbonate in 10.4 ml of water, 0.68 g of lithium chloride, 75 ml of toluene, 25 ml of ethanol and 0.7 g of tetrakis (triphenylphosphine)palladium are stirred, under an inert atmosphere, at relfux for 4 hours. The resulting mixture is filtered, the solvents are evaporated off under reduced pressure and the residue obtained is purified by chromatography on a column of silica gel, eluting with a 99/1 (v/v) dichloromethane/ethanol mixture. The compound obtained is taken up in diethyl ether and hydrogen chloride is bubbled through. The resulting mixture is filtered and the solvents are evaporated off under reduced pressure; m.p.=130° C. (HCl.0.2 H₂O).

The compounds of EXAMPLES 14 and 15 below are prepared in the same way:

TABLE 7

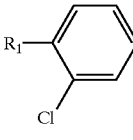

| EXAMPLE | R₁ | m.p.; ° C. (salt, hydrate) |
|---|---|---|
| 14 |  | 155 HCl |
| 15 | 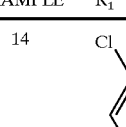 | 139 HCl 0.3 H₂O |

EXAMPLE 16

[3-(4-Adamantan-2-yl-3-chlorophenyl)prop-2-ynyl] cyclohexylethylamine hydro-chloride

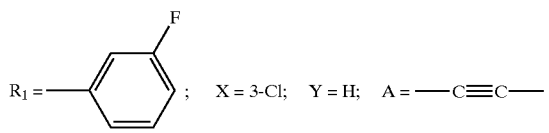

a) 2-{2-chloro-4-[3-(cyclohexylethylamino)prop-1-ynyl]phenyl}adamantan-2-ol

[3-(4-Bromo-3-chlorophenyl)propen-2-ynyl] cyclohexylethylamine hydrochloride is treated with 1 N sodium hydroxide solution in ether to give the base. 30.5 ml of a 15% solution of n-butyllithium in hexane are added, at −75° C., to 17.5 g of [3-(4-bromo-3-chlorophenyl)-propen-2-ynyl]cyclohexylethylamine in 200 ml of diethyl ether, and stirring is continued at −75° C. for 1 hour 30 minutes. Still at −75° C., 7.51 g of amandatan-2-one in 100 ml of diethyl ether are added and the reaction mixture is then stirred for 2 hours at −75° C.

The reaction mixture is allowed to warm to room temperature and stirring is continued for 1 hour. The reaction mixture is hydrolysed and extracted with diethyl ether, the organic phases are dried over magnesium sulphate and the solvents are evaporated off under reduced pressure. The residue obtained is purified by chromatography on a column of silica gel, eluting with a dichloromethane/ethanol mixture varying from 100/0 to 99/1 (v/v). The compound obtained is used directly in the next step.

b) 9.78 g of sodium iodide are added to 11.12 g of the compound obtained above in 50 ml of acetonitrile and 25 ml of dichloromethane, followed by addition of 6.63 ml of chlorotrimethylsilane. The reaction mixture is stirred at 30° C. for 2 hours, followed by addition of 25 ml of acetonitrile, 5.12 g of zinc powder and 2.99 ml of acetic acid. The reaction mixture is heated at 80° C. for 3 hours, allowed to cool to room temperature, filtered, washed with diethyl ether and extracted with dichloromethane, and the solvents are then evaporated off under reduced pressure. The residue obtained is purified by chromatography on a column of silica gel, eluting with a 97/3 (v/v) toluene/ethanol mixture and then with a 92.5/7.5 (v/v) cyclohexane/ethyl acetate mixture. The compound obtained is taken up in diethyl ether and the hydrochloride is prepared by bubbling hydrogen chloride through, and the precipitate obtained is filtered off and dried; m.p.=110° C. (HCl.0.3 H$_2$O).

EXAMPLE 17

{3-[4-(4,4-Dimethylcyclohexyl)-2-chlorophenyl]prop-2-ynyl}cyclohexylethylamine Hydrochloride

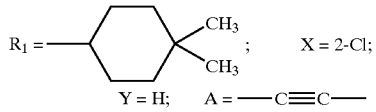

; X = 2-Cl;

Y = H; A = ——C≡C——

(I)

1.42 g of dichlorobis(triphenylphosphine)palladium are added, under an inert atmosphere, to 8.03 g of cyclohexylethylprop-2-ynylamine (compound 4.1), 15 g of [4-(4,4-dimethylcyclohexyl)-2-chlorophenyl] trifluoromethanesulphonate (compound 111.1), 0.19 g of copper iodide, 3.4 g of lithium chloride in 200 ml of triethylamine and 100 ml of pyridine. The reaction mixture is refluxed for 12 hours. The solvents are evaporated off under reduced pressure and the residue obtained is purified by chromatography on a column of silica gel, eluting with a cyclohexane/ethyl acetate mixture varying from 95/5 to 90/10 (v/v). The residue obtained is taken up in diethyl ether. The hydrochloride is separated out by filtration and hydrogen chloride is then bubbled through. The residue obtained is recrystallized from ethyl acetate.

$^1$H NMR: 11 (s, 11H); 7.6–7.4 (m, 2H); 7.3 (d, 1H); 4.3 (s, 2H); 3.2 (m, 2H); 1.5 (m, 1H); 2.2–1.1 (m, 22H); 0.9 (d, 6H).

The compounds of EXAMPLES 18 to 28 below are prepared in the same way:

EXAMPLE 18

[4-(4-Adamantan-2-yl-2-chlorophenyl)but-3-ynyl]cyclohexylethylamine Hydrochloride

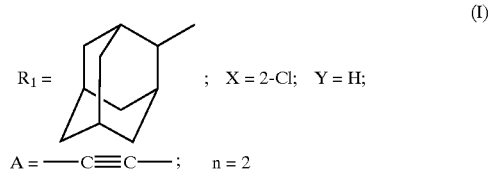

; X = 2-Cl; Y = H;

A = ——C≡C——; n = 2

(I)

$^1$H NMR: 7.5 (d, 1H); 7.4 (s, 1H); 7.3 (d, 1H); 3.4–3.2 (m, 4H); 3.1 (m, 2H); 3.0 (s, 1H); 2.4 (s, 2H); 2.0–2.1 (m, 26H).

TABLE 8

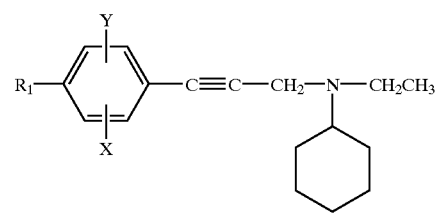

(I)

| EXAMPLE | R$_1$ | X | Y | m.p.; ° C. or $^1$H NMR (salt, hydrate) |
|---|---|---|---|---|
| 19 |  | 3-Cl | 5-Cl | 7.5(d, 1H); 7.2 (d, 1H); 4.3(s, 2H); 3.3 (m, 3H) 2.6–1.1(m, 28H) HCl |
| 20 | 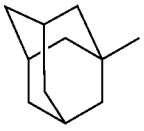 | H | H | 186 HCl 0.8 H$_2$O |
| 21 | 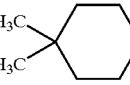 | H | H | 134 |
| 22 | 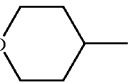 | H | H | 152 HCl |
| 23$^{(a)}$ | 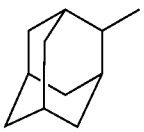 | 3-Cl | 6-Cl | 196 HCl |
| 24 | 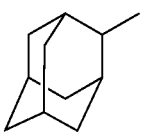 | 3-F | 5-F | 132 HCl |

TABLE 8-continued (I)

R₁—[phenyl ring with Y and X substituents]—C≡C—CH₂—N(cyclohexyl)—CH₂CH₃

| EXAMPLE | R₁ | X | Y | m.p.; °C. or ¹H NMR (salt, hydrate) |
|---|---|---|---|---|
| 25 | 2-hydroxyadamantyl (OH) | 3-Cl | 5-Cl | 210 HCl |

(a)prepared according to the same synthetic scheme as EXAMPLE 17, using 4-bromo-3-methoxyphenol as starting material (J. Am. Chem. Soc. 1926, 48, 3129)

TABLE 9

(I)

adamantyl—[phenyl with Y and X]—C≡C—CH₂—N(cyclohexyl)—CH₂(CH₃)₂

| EXAMPLE | X | Y | Salt | ¹H NMR |
|---|---|---|---|---|
| 26 | H | H | HCl | 10.3(s, 1H); 7.4(m, 4H); 4.3(s, 2H); 3.8(m, 1H); 2.4(s, 2H); 2.1–1.1(m, 30H) |
| 27 | 2-Cl | H | HCl | 10.4(s, 1H); 7.6(d, 1H); 7.5(s, 1H); 7.4(d, 1H); 4.4(s, 2H); 3.8(m, 1H); 3.4(m, 1H); 2.9(s, 1H); 2.4(s, 2H); 2.1–1.2(m, 28H) |
| 28 | 3-Cl | Cl | HCl | 10.3(s, 1H); 7.6(s, 2H); 4.3(s, 2H); 3.5–1.0(m, 32H) |

EXAMPLE 29

{(Z)-3-[3-Chloro-4-(3,3,5,5-tetramethylcyclohexyl) phenyl]propen-2-yl}cyclohexylethylamine Hydrochloride

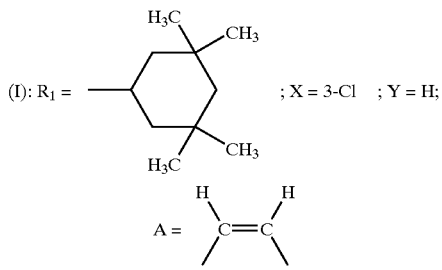

(I): R₁ = 3,3,5,5-tetramethylcyclohexyl; X = 3-Cl; Y = H;

A = \C=C/ (cis, H,H)

3 g of the compound of EXAMPLE 3 in 50 ml of petroleum ether are hydrogenated, under an inert atmosphere and at atmospheric pressure, in the presence of 3 ml of cyclohexene and 0.3 g of palladium on calcium carbonate poisoned with 3.5% lead (Lindlar catalyst). The reaction mixture is filtered through Celite, the solvents are evaporated off and the residue obtained is purified by chromatography on a column of silica gel, eluting with a 95/5 (v/v) dichloromethane/ethanol mixture. The oily residue obtained is taken up in diethyl ether and hydrogen chloride is bubbled through. The precipitate is filtered off and dried under reduced pressure. The compound of EXAMPLE 29 is isolated in a yield of 83%; m.p.=158° C. (HCl.0.1 H₂O).

The compounds of EXAMPLES 30 to 54 given below are prepared in the same way:

TABLE 10

(I)

R₁—[phenyl]—CH=CH—CH₂—N(cyclohexyl)—CH₂—CH₃

| EXAMPLE | R₁ | m.p.; °C. (salt, hydrate) |
|---|---|---|
| 30 | 1,1,3,3-tetramethylcyclohexyl (H₃C, CH₃, H₃C, CH₃) | 170 HCl |
| 31 | adamantyl | 182 HCl |
| 32 | adamantyl (alt) | 138 HCl 0.3 H₂O |
| 33 | 1,1-dimethylcyclohexyl (H₃C, H₃C) | 152 |
| 34 | tetrahydropyran-4-yl (O-containing ring) | 162 HCl |

TABLE 11

(I) Structure: Y-C₆H₃(R₁)(X)-CH=CH-CH₂-N(CH₂CH₃)(cyclohexyl)

| EXAMPLE | R₁ | X | Y | m.p.; °C. (salt, hydrate) |
|---|---|---|---|---|
| 35 | 1,1,3-trimethylcyclohexyl | 3-Cl | H | 155 HCl |
| 36 | 2-adamantyl | 3-Cl | H | 114 HCl 0.5 H₂O |
| 37 | tert-butyl | 3-Cl | H | 144 HCl 0.3 H₂O |
| 38 | 4-fluorophenyl | 3-Cl | H | 105 HCl 1.1 H₂O |
| 39 | 3-fluorophenyl | 3-Cl | H | 108 HCl 0.6 H₂O |
| 40 | 3,5-difluorophenyl | 3-Cl | H | 138 HCl |
| 41 | 4-chlorophenyl | 3-Cl | H | 160 HCl |
| 42 | 4-methoxyphenyl | 3-Cl | H | 70 HCl 0.7 H₂O |
| 43 | 3-chlorophenyl | 3-Cl | H | 102 HCl 0.4 H₂O |

TABLE 11-continued

| EXAMPLE | R₁ | X | Y | m.p.; °C. (salt, hydrate) |
|---|---|---|---|---|
| 44[a] | 2-adamantyl | 3-Cl | 5-Cl | 188 HCl |
| 45[b] | 1,1-dimethylcyclohexyl (4-methyl) | 3-Cl | H | 161 HCl |
| 46 | 1,1-dimethylcyclohexyl (4-methyl) | 2-Cl | H | 195 HCl |

TABLE 12

(I) Structure: adamantyl-C₆H₃(Y)(X)-CH=CH-(CH₂)ₙ-N(R₂)(cyclohexyl) with CH₂CH₃

| EXAMPLE | X | Y | N | R₂ | m.p.; °C. (salt, hydrate) |
|---|---|---|---|---|---|
| 47 | H | H | 1 | —CH(CH₃)₂ | (a) HCl |
| 48 | 3-Cl | H | 1 | —CH(CH₃)₂ | HCl 0.75 H₂O |
| 49 | 3-Cl | 5-Cl | 1 | —CH(CH₃)₂ | 226 HCl |
| 50 | 2-Cl | H | 1 | —CH(CH₃)₂ | 162 HCl; H₂O |
| 51[b] | 3-Cl | 5-Cl | 1 | —CH₃ | 204 |
| 52 | 3-Cl | 5-Cl | 2 | —CH₂CH₃ | 90 HCl; 0.2 H₂O |

[a] mass ES⁺: 392.4 (MH⁺); 251.3 and 135.3
[b] prepared according to the same synthetic scheme as in EXAMPLE 44, using compound 4.2 as starting material.

EXAMPLE 53

[(Z)-3-(2,6-Dichlorobiphenyl-4-yl)propen-2-yl]cyclohexylethylamine Hydrochloride

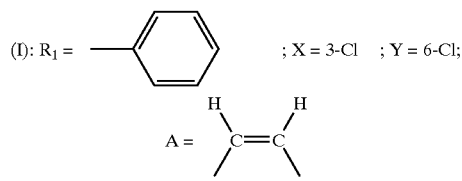

m.p.=120° C. (HCl).

EXAMPLE 54

[(Z)-4-(4-Adamantan-2-yl-3-chlorophenyl)but-3-ynyl]cyclohexylethylamine Hydrochloride

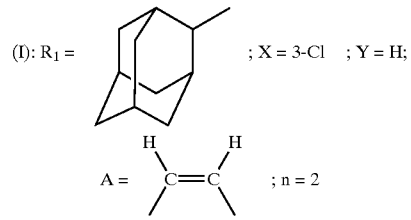

m.p.=178° C, (HCl).

The compounds in TABLE 13 below are prepared according to the same synthetic scheme as that in EXAMPLE 44:

TABLE 13

| EXAMPLE | X | Y | $R_1$ | $R_2$ | m.p.; °C. salt, hydrate |
|---|---|---|---|---|---|
| 55 | 3-F | 5-F | adamantyl | $-C_2H_5$ | 182 HCl |
| 56[a] | 3-OCH$_3$ | H | adamantyl | $-C_2H_5$ | gum HOC(O)CF$_3$ |
| 57 | 3-Cl | 5-Cl | adamantyl-OH | $-C_2H_5$ | 210 HCl 0.2 H$_2$O |
| 58 | 3-Cl | 6-Cl | adamantyl | $-C_2H_5$ | 165 HCl |
| 59 | 3-Cl | —H | dicyclopropylmethyl | $-C_2H_5$ | 140 HCl |
| 60[b] | 2-Cl | 6-Cl | adamantyl | $-C_2H_5$ | 174 HCl |
| 61 | —H | —H | 3,5-dimethylcyclohexyl | $-C_2H_5$ | 142 HCl |
| 62 | 2-Cl | —H | adamantyl | $-C_2H_5$ | 208 HCl |
| 63 | 3-Cl | 5-Cl | adamantyl | —H | 152 HCl |

[a]using 4-bromo-3-methoxyphenol as starting material (J. Am. Chem. Soc. 1926, 48, 3129)
[b]using 4-bromo-2,6-dichlorophenol as starting material (J. Am. Chem. Soc 1933, 55, 2125–2126)

EXAMPLE 64

{(E)-3-[3-chloro-4-(3,3,5,5-tetramethylcyclohexyl)phenyl]propen-2-yl}cyclohexylethylamine Hydrochloride (I): $R_1$ = 3,3,5,5-tetramethylcyclohexyl ; X = 3-Cl ; Y = H;

-continued

A = 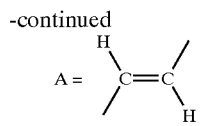

24.3 ml of a 1 M solution of diisobutylaluminium hydride (DIBALH) in toluene are added dropwise under an inert atmosphere to a solution of 4 g of the compound of EXAMPLE 4 in 40 ml of toluene. The reaction mixture is stirred at 40° C. for 1 hour and is then poured into a water/ice mixture and sodium hydroxide is added until a pH equal to 7 is obtained. The resulting mixture is extracted with dichloromethane, the phases are separated after settling has taken place, the organic phase is dried over magnesium sulphate and the solvents are evaporated off under reduced pressure. The residue is taken up in diethyl ether and hydrogen chloride is bubbled through. The precipitate obtained is filtered off and dried; m.p.=169° C. (HCl.0.2 H$_2$O).

The compounds of EXAMPLES 65 to 67 below are prepared according to the procedure described for EXAMPLE 64.

EXAMPLE 65

{(E)-3-[4-(3,3,5,5-Tetramethylcyclohexyl)phenyl]propen-2-yl}cyclohexylethylamine Hydrochloride

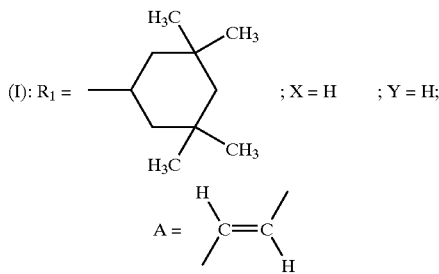

m.p.=200° C. (HCl).

EXAMPLE 66

{(E)-3-[4-(2-Adamantyl)phenyl]propen-2-yl}cyclohexylethylamine Hydrochloride

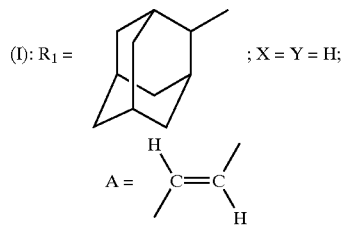

m.p.=200° C. (HCl)

EXAMPLE 67

{(E)-3-[4-(2-Adamantyl)-3,5-dichlorophenyl]propen-2-yl}cyclohexylethylamine Hydrochloride

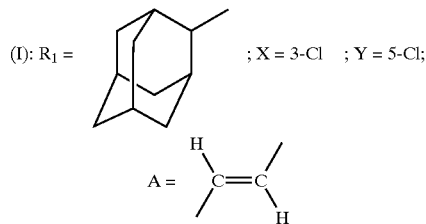

m.p.=224° C. (HCl)

EXAMPLE 68

{3-[3-Chloro-4-(3,3,5,5-tetramethylcyclohexyl)phenyl]propyl}cyclohexylethylamine Hydrochloride

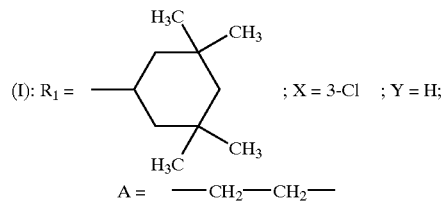

4 g of the compound of EXAMPLE 3 are hydrogenated in the presence of 0.4 g of 10% palladium on charcoal and 50 ml of ethanol. The reaction mixture is filtered, the filtrate is evaporated under reduced pressure and the residue obtained is purified on a column of silica gel, eluting with a 97/3 (v/v) toluene/ethanol mixture. The oily residue obtained is taken up in diethyl ether and hydrogen chloride is bubbled through. The precipitate obtained is filtered off and dried; m.p.=154° C. (HCl).

The compounds of EXAMPLES 69 to 78 given below are prepared in the same way:

TABLE 14

(I)

| EXAMPLE | R$_1$ | X | m.p.; ° C. (salt, hydrate) |
|---|---|---|---|
| 69 | 3,3,5,5-tetramethylcyclohexyl | H | 170 HCl 0.2 H$_2$O |

TABLE 14-continued (I)

![Structure showing R1-phenyl(X)-CH2-CH2-CH2-N(cyclohexyl)-CH2-CH3]

| EXAMPLE | R₁ | X | m.p.; °C. (salt, hydrate) |
|---|---|---|---|
| 70 | adamantyl | H | 182 HCl 0.6 H₂O |
| 71 | 4-F-phenyl | Cl | 129 HCl |
| 72 | 1,4-dimethylcyclohexyl (H₃C, CH₃) | Cl | 184 HCl |
| 73 | 3-Cl-phenyl | Cl | 102 HCl 1.2 H₂O |
| 74 | 3,4-diF-phenyl | Cl | 104 HCl |
| 75 | 3-F-phenyl | Cl | 88 HCl 0.7 H₂O |
| 76 | adamantyl | H | 228 HCl |

EXAMPLE 77

[3-(2,6-Dichlorophenyl-4-yl)propyl]
cyclohexylethylamine hydrochloride

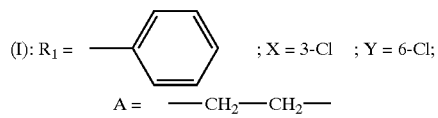

(I): R₁ = phenyl ; X = 3-Cl ; Y = 6-Cl;

A = —CH₂—CH₂— m.p.=128° C. (HCl)

EXAMPLE 78

{-3-[4-(2-Adamantyl)-3,5-dichlorophenyl]
propyl}cyclohexylethylamine Hydrochloride

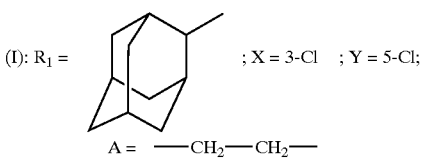

(I): R₁ = 2-adamantyl ; X = 3-Cl ; Y = 5-Cl;

A = —CH₂—CH₂— m.p.F=220° C. (HCl)

What is claimed is:

1. A compound of formula:

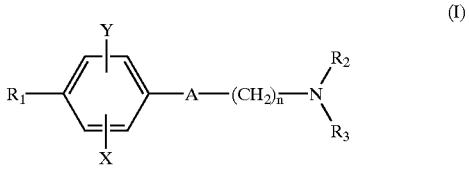

in which:

A represents a group chosen from the following:
—C≡C—, —CH=CH—; —CH₂—CH₂— n is equal to 1 or 2;

X represents a hydrogen, chlorine or fluorine atom or a methyl or methoxy group;

Y represents a hydrogen atom or a chlorine or fluorine atom;

$R_1$ represents a cyclohexyl group monosubstituted, disubstituted, trisubstituted or tetrasubstituted with a methyl group; a phenyl group monosubstituted or disubstituted with a fluorine or chlorine atom or with a methoxy group; a cycloheptyl, tert-butyl, dicyclopropylmethyl, bicyclo[3.2.1]octanyl, 4-tetrahydropyranyl, 4-tetrahydrothiopyranyl or 1- or 2-adamantyl or adamantan-2-ol group; or $R_1$ represents a phenyl group, it being understood that, in this case, X and Y are other than hydrogen;

$R_2$ represents a hydrogen atom or a ($C_1$–$C_4$)alkyl group optionally substituted with a trifluoromethyl group;

$R_3$ represents a ($C_5$–$C_7$)cycloalkyl;

and the addition salts of these compounds with pharmaceutically acceptable acids, as well as the solvates and hydrates thereof.

2. A compound according to claim 1 in which:

A represents a group chosen from the following:
—C≡C—, —CH=CH—; —CH₂—CH₂— n is equal to 1 or 2;

X represents a hydrogen, chlorine or fluorine atom or a methyl or methoxy group;

Y represents a hydrogen atom or a chlorine or fluorine atom;

$R_1$ represents a cyclohexyl group monosubstituted, disubstituted, trisubstituted or tetrasubstituted with a methyl group; a phenyl group monosubstituted or disubstituted with a fluorine or chlorine atom or with a methoxy group; a cycloheptyl, tert-butyl, dicyclopropylmethyl, bicyclo[3.2.1]octanyl, 4-tetrahydropyranyl, 4-tetrahydrothiopyranyl or 1- or 2-adamantyl group; or $R_1$ represents a phenyl group, it being understood that, in this case, X and Y are other than hydrogen;

R$_2$ represents a (C$_1$–C$_4$)alkyl optionally substituted with a trifluoromethyl group;

R$_3$ represents a (C$_5$–C$_7$)cycloalkyl;

and the addition salts of these compounds with pharmaceutically acceptable acids, as well as the solvates and hydrates thereof.

3. A compound according to claim 1 of formula:

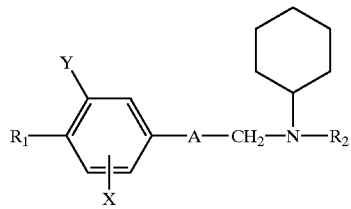

(I.1)

in which:

A represents a group chosen from the following:
—C≡C—, —CH=CH—; —CH$_2$—CH$_2$—

X represents a hydrogen or chlorine atom;

Y represents a hydrogen atom or a chlorine atom;

R$_1$ represents a cyclohexyl monosubstituted, disubstituted, trisubstituted or tetrasubstituted with a methyl group; a phenyl group substituted with a chlorine atom, a methoxy group or one or two fluorine atoms; a tert-butyl or 1- or 2-adamantyl group; or R$_1$ represents a phenyl group, it being understood that, in this case, X and Y both represent a chlorine atom;

R$_2$ represents a (C$_2$–C$_3$)alkyl;

and the addition salts of these compounds with pharmaceutically acceptable acids, as well as the solvates and hydrates thereof.

4. A compound according to claim 3 in which A represents a —CH=CH— group of (Z) configuration.

5. A compound according to claim 4 in which X represents a chlorine atom and Y represents a hydrogen or chlorine atom.

6. A compound according to claim 5 in which R$_1$ represents a 3,3,5,5-tetramethylcyclohexyl or 3,3-dimethylcyclohexyl or 4,4-dimethylcyclohexyl group, a phenyl group monosubstituted or disubstituted with a fluorine atom or substituted in position 4 with a chlorine atom; or a 1- or 2-adamantyl group.

7. A compound according to claim 1, chosen from:

[(Z)-3-(4-Adamantan-2-yl-3-chlorophenyl)propen-2-yl]cyclohexylethylamine;

[(Z)-3-(4-Adamantan-2-ylphenyl)propen-2-yl]cyclohexylethylamine;

{(Z)-3-[4-(4,4-Dimethylcyclohexyl)-2-chlorophenyl]propen-2-yl}cyclohexylethylamine;

[(Z)-3-(4-Adamantan-1-yl-3-chlorophenyl)propen-2-yl]cyclohexylethylamine;

[(Z)-3-(4-Adamantan-2-yl-3,5-dichlorophenyl)propen-2-yl]cyclohexylethylamine;

[(Z)-3-(4-Adamantan-2-yl-3,5-dichlorophenyl)propen-2-yl]cyclohexyl(2-methylethyl)amine;

as well as the salts thereof with pharmaceutically acceptable acids and the solvates and hydrates thereof.

8. [(Z)-3-(4-Adamantan-2-yl-3,5-dichlorophenyl)propen-2-yl]cyclohexylethylamine as well as the salts thereof with pharmaceutically acceptable acids, solvates thereof and hydrates thereof according to claim 7.

9. A process for preparing a compound according to claim 1, in which A represents a —C≡C— group wherein:

a) either, if n=1, a Mannich reaction is carried out between the phenylacetylene derivative of formula:

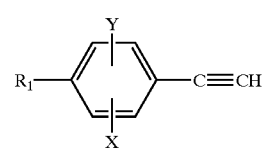

(II)

in which R$_1$, X and Y are as defined for (I), the formaldehyde and the amine (1) HNR$_2$R$_3$, R$_2$ and R$_3$ being as defined for (I);

b) or, a Suzuki coupling is carried out between the compound of formula:

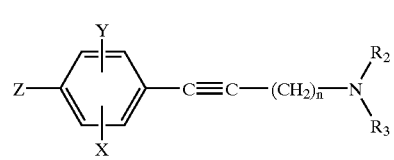

(Ia)

in which X, Y, n, R$_2$ and R$_3$ are as defined for (I) and Z represents a bromine, an iodine or a trifluoromethanesulphonate (OTf) group and a boron derivative (2) of formula R$_1$—B(OR)$_2$ in which R represents a hydrogen atom or an alkyl or aryl group in the presence of a base and a metal catalyst;

c) or, when R$_1$ represents a cyclohexyl group monosubstituted, disubstituted, trisubstituted or tetrasubstituted with a methyl group; a cycloheptyl, 4-tetrahydropyranyl, 4-tetrahydrothiopyranyl or adamantyl group, a coupling is carried out between compound (Ia) in which Z represents an iodine or bromine atom and the ketone (3) corresponding to R$_1$ represented by

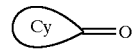

in the presence of a base, to give the intermediate compound of formula:

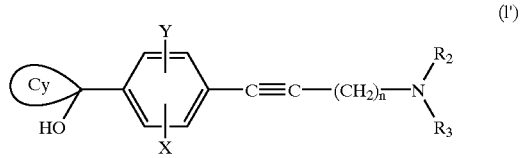

(I')

in which X, Y, n, R$_2$ and R$_3$ are as defined for (I); the said compound (I') then being reduced under selective conditions;

d) or, a coupling reaction is carried out between the amine of formula:

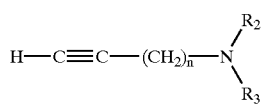

(4)

in which n, $R_2$ and $R_3$ are as defined for (I), and the compound of formula:

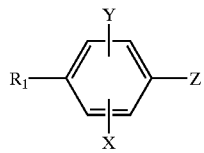

(III)

in which $R_1$, X and Y are as defined for (I) and Z represents a bromine or iodine atom or a trifluoromethylsulphonate (triflate or OTf) group.

10. A process for preparing a compound according to claim 1, in which A represents a —CH=CH— group wherein a hydrogenation is carried out, with nascent hydrogen or in the presence of cyclohexene, of compound (I) in which A represents an acetylene group —C≡C—, in order to prepare the ethylenic compound (I) in the form of a mixture of the Z and E isomers, or this hydrogenation is carried out in the presence of a metal catalyst on a support in order to prepare the ethylenic compound (I) in Z form, or alternatively compound (I) in which A represents an acetylene group —C≡C— is reacted with a metal hydride in order to prepare the ethylenic compound (I) in E form.

11. A process for preparing a compound according to claim 1, in which A represents a —CH$_2$—CH$_2$-group wherein a hydrogenation of compound (I), in which A represents a —CH=CH— or —C≡C— group, is carried out.

12. A pharmaceutical composition containing, as active principle, a compound according to any one of claims 1 to 8.

13. A method for treating conditions in which it is desirable to reduce the immunological activity which comprises administering to a patient in need of such treatment an effective amount of a compound according to any one of claims 1 to 8.

14. A method for combating the proliferation of tumour cells which comprises administering to a patient in need of such treatment an effective amount of a compound according to any one of claims 1 to 8.

15. A method for treating heart rate disorders which comprises administering to a patient in need of such treatment an effective amount of a compound according to any one of claims 1 to 8.

* * * * *